US010081678B2

(12) United States Patent
Li

(10) Patent No.: US 10,081,678 B2
(45) Date of Patent: Sep. 25, 2018

(54) SPECIFIC BINDING ANTIBODIES OF GLYCOPROTEIN IB ALPHA AS SELECTIVE ECTODOMAIN SHEDDING INHIBITORS

(71) Applicants: EMORY UNIVERSITY, Atlanta, GA (US); CHILDREN'S HEALTHCARE OF ATLANTA, INC., Atlanta, GA (US)

(72) Inventor: Renhao Li, Decatur, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 210 days.

(21) Appl. No.: 14/764,541

(22) PCT Filed: Feb. 3, 2014

(86) PCT No.: PCT/US2014/014377
§ 371 (c)(1),
(2) Date: Jul. 29, 2015

(87) PCT Pub. No.: WO2014/121176
PCT Pub. Date: Aug. 7, 2014

(65) Prior Publication Data
US 2016/0009801 A1 Jan. 14, 2016

Related U.S. Application Data

(60) Provisional application No. 61/760,249, filed on Feb. 4, 2013.

(51) Int. Cl.
C07K 16/28 (2006.01)
A61K 39/395 (2006.01)
C07K 16/40 (2006.01)

(52) U.S. Cl.
CPC .......... *C07K 16/28* (2013.01); *C07K 16/2896* (2013.01); *C07K 16/40* (2013.01); *C07K 2317/24* (2013.01); *C07K 2317/33* (2013.01); *C07K 2317/35* (2013.01); *C07K 2317/55* (2013.01); *C07K 2317/565* (2013.01); *C07K 2317/70* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,173,595 B2 | 5/2012 | Dai | |
| 2003/0215785 A1* | 11/2003 | Goodrich | A01N 1/02 435/2 |
| 2005/0019743 A1* | 1/2005 | Wagner | A61K 31/00 435/1.1 |
| 2010/0209423 A1* | 8/2010 | Graus | C07K 16/2854 424/133.1 |
| 2011/0217318 A1 | 9/2011 | Takayama | |
| 2013/0216513 A1 | 8/2013 | Salas | |

FOREIGN PATENT DOCUMENTS

| | | |
|---|---|---|
| WO | 2004105837 | 12/2004 |
| WO | 20110162831 | 12/2011 |
| WO | 2013096932 | 6/2013 |

OTHER PUBLICATIONS

Written Opinion of the International Searching Authority of PCT/US2014/014377 (dated Aug. 4, 2015).*
Rudikoff et al. ,Proc Natl Acad Sci USA 79: 1979-1983 (1982). (Year: 1982).*
Colman, Research in Immunology 145: 33-36 (1994) (Year: 1994).*
Kussie et al., J. Immunol. 152: 146-152 (1994). (Year: 1994).*
Chen et al., EMBO J., 14: 2784-2794 (1995). (Year: 1995).*
Bergmeier et al. Metalloproteinase inhibitors improve the recovery and hemostatic function of in vitro-aged or-injured mouse platelets, Blood, 2003, vol. 102, No. 12, 4229-4235.
Berndt et al. Ristocetin-Dependent Reconstitution of Binding of von Willebrand Factor to Purified Human Platelet Membrane Glycoprotein Ib-IX Complex1, Biochemistry, vol. 27, No. 2, 633-640, 1988.
Canault et al. p38 mitogen-activated protein kinase activation during platelet storage: consequences for platelet recovery and hemostatic function in vivo, Blood, 2010, vol. 115, No. 9, 1835-1842.
Chen et al. Inhibiting GPIbα Shedding Preserves Post-Transfusion Recovery and Hemostatic Function of Platelets After Prolonged Storage, Arterioscler Thromb Vasc Biol. 2016, 36:1821-1828.
Clemetson et al. Platelet GPIb complex as a target for anti-thrombotic drug development, Thromb Haemost 2008; 99: 473-479.
Dai et al. Prolonged inhibition of protein kinase A results in metalloproteinase-dependent platelet GPIbα shedding, Thrombosis Research 124 (2009) 101-109.
Fontayne et al. Rational humanization of the powerful antithrombotic anti-GPIbα antibody: 6B4, Thromb Haemost 2006; 96: 671-84.
Gardiner et al. Controlled shedding of platelet glycoprotein (GP)VI and GPIb-IX-V by ADAM family metalloproteinases, J Thromb Haemost 2007; 5: 1530-7.

(Continued)

*Primary Examiner* — Phillip Gambel
(74) *Attorney, Agent, or Firm* — Klarquist Sparkman, LLP

(57) ABSTRACT

This disclosure relates to specific binding agents, such as isolated recombinant monoclonal antibodies, that bind Glycoprotein Ib alpha (GPIbα). More specifically, the disclosure relates to methods of preventing platelet ectodomain shedding, preventing platelet clearance and degradation, maintaining and increasing platelet blood serum levels for in vitro or in vivo applications. In some embodiments, the disclosure relates to the production, diagnostic use, and therapeutic use of monoclonal and polyclonal antibodies, and the antigen-binding fragments thereof, which specifically bind GPIbα. Aspects of the disclosure also relate to hybridomas or other cell lines expressing such antibodies for specific binding agent. Compositions and methods for inhibiting shedding, clearance, or degradation, or treating diseases associated with GPIba ectodomain shedding are also described.

18 Claims, 9 Drawing Sheets
Specification includes a Sequence Listing.

(56) References Cited

OTHER PUBLICATIONS

GenBank: AAA39002.1, Ig kappa-chain, partial [Mus musculus]. https://www.ncbi.nlm.nih.gov/protein/AAA39002.1, Printed Sep. 13, 2017, 4:17 PM.
Gitz et al. Improved platelet survival after cold storage by prevention of glycoprotein Ibα clustering in lipid rafts. Haematologica 2012, 97(12):1873-1881.
Liang et al. Specific inhibition of ectodomain shedding of glycoprotein Ibα by targeting its juxtamembrane shedding cleavage site, J Thromb Haemost 2013,11: 2155-62.
Mo et al. Transmembrane and Trans-subunit Regulation of Ectodomain Shedding of Platelet Glycoprotein Ib alpha, The Journal of Biological Chemistry vol. 285, No. 42, pp. 32096-32104, 2010.
Nurden et al. Inherited platelet disorders, Haemophilia (2012), 18 (Suppl. 4), 154-160.
Tao et al. Structural basis for the specific inhibition of glycoprotein Ibα shedding by an inhibitory antibody, Scientific Reports, 2016, 6:24789.

* cited by examiner

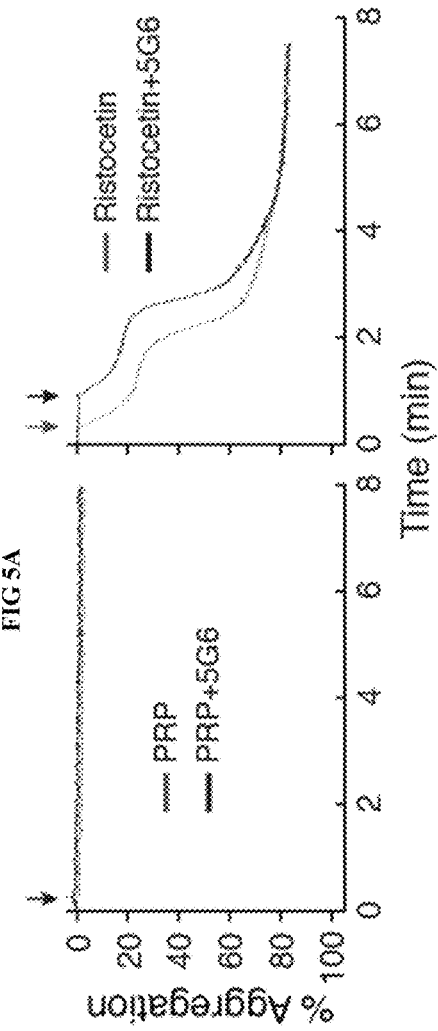
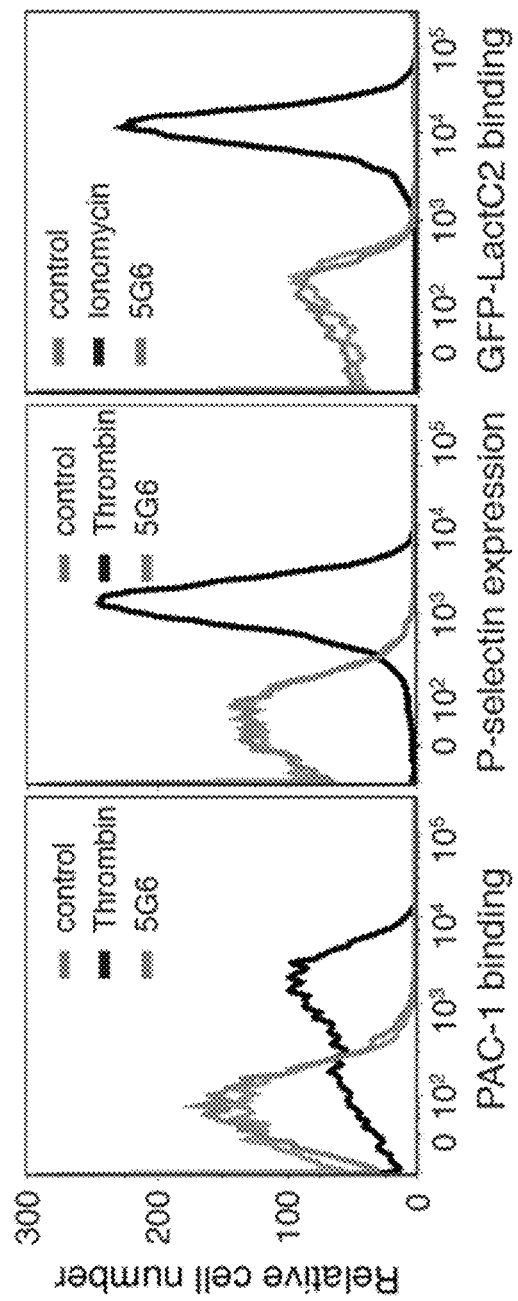
FIG 5A
FIG 5B

| 1H5.C3 SEQ ID:74 SEQ ID:1 w/o Leader | H1 | MDFGLSLVFLVLILKGVQCEVKLVESGGGLVKPGGSLKLSCAASGF AFSSYDMSWVRQTPEKRLEWVATISSGGSYTFYPESVKGRITVYRD NARNTLYLQMSSLRSEDTALYYCATLHYNYERGAVDYWGQGTSV TVSSATTTAPSVYPL |
|---|---|---|
| 2B9.B2 SEQ ID:75 SEQ ID:2 w/o Leader | H2 | MAWVWTLLFLMAAAQSIQAQIQLVQSGPELKKPGETVKISCKASG YTFTDYAMHWVKQAPAKGLKWMGWINTETGEPTYADDFKGRFA FSLETSASTAYLQINNLKNEDTATYFCAGDPLDYWGQGTTLTVSS |
| 2D2.E3 SEQ ID:76 SEQ ID:3 w/o Leader | H3 | MAWVWTLLFLMAAAQSIQAQIQLVQSGPELKKPGETVKISCKASG YTFTDYAMHWVKQAPAKGLKWMGWINTETGEPTYADDFKGRFA FSLETSASTAYLQINNLKNEDTATYFCAGDPLDYWGQGTTLTVSS |
| 3D1.C1 SEQ ID:77 SEQ ID:4 w/o Leader | H4 | MAWVWTLLFLMAAAQSIQAQIQLVQSGPELKKPGETVKISCKASG YTFTDFAMHWVKQAPRKGLKWMGWINTETGEPTYADDFKGRFA FSLGTSASTAFLQINNLKNEDTATYFCSSDPLDYWGQGTTLTVSS |
| 15C6.D3 SEQ ID:78 SEQ ID:5 w/o Leader | H5 | MGRLTFSFLLLIVPAYVLCQVTLKESGPGILQPSQTLSLTCSFSGFSL STSNMGVVWIRQSSGKGLEWLLHILWNDGKFYNPALKSRLTISKD TYNNQVFLKIANVDTADTATYYCARLFSTTTSGYFDVWGAGTTVT VSS |
| 5G6.B4 SEQ ID:79 SEQ ID:6 w/o Leader | H6 | MGRLTFSFLLLIVPAYVLCQVTLKESGPGILQPSQTLSLTCSFSGFSL STSNMGVVWIRQPSGKGLEWLLHILWNDGKFYNPALKSRLTISKD TYNNQVFLKIANVDTADTATYYCARLFTTTTSGYFDVWGAGTTVT VSS |

FIG. 6

| | | |
|---|---|---|
| 1H5.C3 SEQ ID: 54 SEQ ID:7 w/o Leader | L1 | IVIRLTIGRIEFSGREFALDVVVTQTPSSMYASLGERVSITCKASQDI NRYLSWIQQKPGKSPKTLIYRTDRLVEGAPSRFSGSGSGQDYSLTIS SLEYEDMGIYNCLQYDEFPVTFGAGTKLEIKRKSTAPTVSKGEFV |
| 2B9.B2 SEQ ID: 55 SEQ ID:8 w/o Leader | L2 | MNLPVHLLVLLLFWIPASRGDVVVTQTPLSLPVSFGDQVSISCRSSQ SLANSYGNTYLSWYLHKPGQSPQLLIYEISNRFSGVSDRFSGSGSGT DFTLKISTIKPEDLGIYYCLQGTHQPWTFGGGTKLEIK |
| 2D2.E3 SEQ ID: 56 SEQ ID:9 w/o Leader | L3 | MNLPVHLLVLLLFWIPASRGDVVVTQTPLSLPVSFGDQVSISCRSSQ SLANSYGNTYLSWYLHKPGQSPQLLIYEISNRFSGVSDRFSGSGSGT DFTLKISTIKPEDLGIYYCLQGTHQPWTFGGGTKLEIK |
| 3D1.C1 SEQ ID: 57 SEQ ID:10 w/o Leader | L4 | MNLPVHLLVLLLFWIPASRGDVVVTQTPLSLPVSFGDQVSISCRSSQ SLTNSYGNTYLSWFLHKPGQSPQLLIYEISNRFSGVPDRFSGSGSGT DFTLKISTIKPEDLGIYYCLQGTHQPWTFGGGTKLEIK |
| 15C6.D3 SEQ ID: 58 SEQ ID:11 w/o Leader | L5 | MSVLTQVLALLLLWLTGARCDIQMTQSPASLSASVGETVTITCRAS GNIHNYLAWYQQKQGKSPQLLVYNAETLADGVPSRFSGSESGTQ YSLKINSLQPEDFGTYYCQHFWDTPWTFGGGTKLEIK |
| 5G6.B4 SEQ ID: 59 SEQ ID:12 w/o Leader | L6 | MSVLTQVLALLLLWLTGARCDIQMTQSPASLSASVGETVTITCRAS GNIYNYLAWYQQKQGKSPQLLVYNAKTLADGVPSRFSGSGSGTQ YSLKINSLQPEDFGSYFCQHFWDTPWTFGGGTKLEIK |

FIG. 7

Clone 2B9.B2, IgG2b

- Heavy Chain DNA Sequence
  - <u>ATGGCTTGGGTGTGGACCTTGCTATTCCTGATGGCAGCTGCCCAAAGTATCCAAGCACAG</u>ATCCAGTTGGTGCAGTCTGGACCTGAGCTGAAGAAGCCTGGAGAGACAGTCAAGATCTCCTGCAAGGCTTCT<u>GGTTATACCTTCACAGACTATGCAATGCAC</u>TGGGTGAAGCAGGCTCCAGCAAAGGGTTTAAAGTGGATGGGC<u>TGGATAAACACTGAGACTGGTGAGCCAACATATGCAGATGACTTCAAGGGA</u>CGGTTTGCCTTCTCTTTGGAAACCTCTGCCAGCACTGCCTATTTACAGATCAACAACCTCAAAAATGAGGACACGGCAACATATTTCTGTGCTGGC<u>GACCCTCTTGACTA</u>CTGGGGCCAGGGCACCACTCTCACAGTCTCCTCA (SEQ ID NO. 60) (without leader sequence SEQ ID: 44)
- Heavy Chain AA Sequence
  - <u>MAWVWTLLFLMAAAQSIQA</u>QIQLVQSGPELKKPGETVKISCKAS<u>GYTFTDYAMH</u>WVKQAPAKGLKWMG<u>WINTETGEPTYADDFKG</u>RFAFSLETSASTAYLQINNLKNEDTATYFCAG<u>DPLDY</u>WGQGTTLTVSS (SEQ ID: 61) (without leader sequence SEQ ID NO. 2)
- Light Chain 1 DNA Sequence
  - <u>ATGAATTTGCCTGTTCATCTCTTGGTGCTTCTGTTGTTCTGGATTCCTGCTTCCAGAGGTGA</u>TGTTGTGGTGACTCAAACTCCACTCTCCCTGCCTGTCAGCTTTGGAGATCAAGTTTCTATCTCTTGC<u>AGGTCTAGTCAGAGTCTTGCAAACAGTTATGGGAACACCTATTTGTCT</u>TGGTACCTACACAAGCCTGGCCAGTCTCCACAGCTCCTCATCTAT<u>GAGATTTCCAACAGATTTTCT</u>GGGGTGTCAGACAGGTTCAGTGGCAGTGGTTCAGGGACAGATTTCACACTCAAGATCAGCACAATAAAGCCTGAGGACTTGGGAATATATTACTGC<u>TTACAAGGTACACATCAGCCGTGGACG</u>TTCGGTGGAGGCACCAAGCTGGAAATCAAA (SEQ ID: 62) (without leader sequence SEQ ID NO. 45)
- Light Chain 1 AA Seq
  - <u>MNLPVHLLVLLLFWIPASRG</u>DVVVTQTPLSLPVSFGDQVSISC<u>RSSQSLANSYGNTYLS</u>WYLHKPGQSPQLLIY<u>EISNRFS</u>GVSDRFSGSGSGTDFTLKISTIKPEDLGIYYC<u>LQGTHQPWT</u>FGGGTKLEIK (SEQ ID: 63) (without leader sequence SEQ ID NO. 8)
- Light Chain 2 DNA Sequence
  - <u>ATGGAATCACAGACTCTGGTCTTCATATCCATACTGCTCTGGTTATATGGAGCTGATGGGA</u>ACATTGTAATGACCCAATCTCCCAAATCCATGTCCATGTCAGTAGGAGAGAGGGTCACCTTGACCTGC<u>AAGGCCAGTGAGAATGTGGTTACTTATGTTTCC</u>TGGTATCAACAGAAACCAGAGCAGTCTCCTAAACTGCTGATATAC<u>GGGGCATCCAACCGGTACACT</u>GGGGTCCCCGATCGCTTCACAGGCAGTGGATCTGCAACAGATTTCACTCTGACCATCAGCAGTGTGCAGGCTGAAGACCTTGCAGATTATCACTGT<u>GGACAGGGTTACAGCTATCCGTACACG</u>TTCGGAGGGGGGACCAAGCTGGAAATAAAA (SEQ ID: 64) (without leader sequence SEQ ID NO. 46)
- Light Chain 2 AA Sequence
  - <u>MESQTLVFISILLWLYGADG</u>NIVMTQSPKSMSMSVGERVTLTC<u>KASENVVTYVS</u>WYQQKPEQSPKLLIY<u>GASNRYT</u>GVPDRFTGSGSATDFTLTISSVQAEDLADYHC<u>GQGYSYPYT</u>FGGGTKLEIK (SEQ ID: 65) (without leader sequence SEQ ID NO. 47)

FIG. 8

Clone 1H5.C3, IgG3

- Heavy Chain DNA Sequence
  - ATGAACTTTGGGCTGAGCTTGATTTTCCTTGTCCTAATTTTAAAAGGTGTCCAGTGTGAAG
    TGAAGCTGGTGGAGTCAGGGGGAGGCTTAGTGAAGCCTGGAGGGTCCCTGAAACTCTCCT
    GTGCAGCCTCT<u>GGATTCGCCTTCAGTAGCTATGACATG</u>TCTTGGGTTCGCCAGACTCCGGA
    GAAGAGGCTGGAGTGGGTCGCA<u>ACCATTAGTAGTGGTGGTAGTTACACCTTCTATCCAGA
    AAGTGTGAAGGGC</u>CGAATCACCGTCTACAGAGACAATGCCAGGAACACCCTGTACCTGCA
    AATGAGCAGTCTGCGGTCTGAGGACACGGCCTTGTATTACTGTGCAACC<u>CTCCATTATAAT
    TACGAGAGGGGTGCTGTGGACTAC</u>TGGGGTCAAGGAACCTCAGTCACCGTCTCCTCA (SEQ ID: 66) (without leader sequence SEQ ID NO. 48)
- Heavy Chain AA Sequence
  - MNFGLSLIFLVLILKGVQCEVKLVESGGGLVKPGGSLKLSCAAS<u>GFAFSSYDMS</u>WVRQTPEKR
    LEWVA<u>TISSGGSYTFYPESVKG</u>RITVYRDNARNTLYLQMSSLRSEDTALYYCATL<u>HYNYERGA
    VDY</u>WGQGTSVTVSS (SEQ ID: 67) (without leader sequence SEQ ID NO. 16)
- Light Chain 1 DNA Sequence
  - ATGAGGACCCCTGCTCAGTTTCTTGGAATCTTGTTGCTCTGGTTTCCAGGTATCAAATGTG
    ACATCAAGATGACCCAGTCTCCATCTTCCATGTATGCATCTCTAGGAGAGAGAGTCAGTAT
    CACTTGC<u>AAGGCGAGTCAGGACATTAATAGGTATTTAAGC</u>TGGATCCAGCAGAAACCAGG
    AAAAATCTCCTAAGACCCTGATCTAT<u>CGTACAGACAGATTGGTAGAG</u>GGGGCCCCATCAAG
    GTTCAGTGGCAGTGGATCTGGGCAAGATTATTCTCTCACCATCAGCAGCCTGGAGTATGA
    AGATATGGGAATTTATAATTGT<u>CTACAGTATGATGAGTTTCCGGTCACG</u>TTCGGTGCTGGG
    ACCAAGCTGGAGCTGAAA (SEQ ID: 68) (without leader sequence SEQ ID NO. 49)
- Light Chain 1 AA Seq
  - MRTPAQFLGILLLWFPGIKCDIKMTQSPSSMYASLGERVSITC<u>KASQDINRYLSW</u>IQQKPGKSP
    KTLIY<u>RTDRL</u>VEGAPSRFSGSGSGQDYSLTISSLEYEDMGIYNC<u>LQYDEFPVT</u>FGAGTKLELK
    (SEQ ID: 69) (without leader sequence SEQ ID NO. 15)
- Light Chain 2 DNA Sequence
  - ATGGAATCACAGACTCTGGTCTTCATATCCATACTGCTCTGGTTATATGGAGCTGATGGGA
    ACATTGTAATGACCCAATCTCCCAAATCCATGTCCATGTCAGTAGGAGAGAGGGTCACCTT
    GACCTGC<u>AAGGCCAGTGAGAATGTGGTTACTTATGTTTCC</u>TGGTATCAACAGAAACCAGA
    GCAGTCTCCTAAACTGCTGATATAC<u>GGGGCATCCAACCGGTACACT</u>GGGGTCCCCGATCG
    CTTCACAGGCAGTGGATCTGCAACAGATTTCACTCTGACCATCAGCAGTGTGCAGGCTGA
    AGACCTTGCAGATTATCACTGT<u>GGACAGGGTTACAGCTATCCGTACACG</u>TTCGGAGGGGG
    GACCAAGCTGGAAATAAAA (SEQ ID: 70) (without leader sequence SEQ ID NO. 50)
- Light Chain 2 AA Seq
  - MESQTLVFISILLWLYGADGNIVMTQSPKSMSMSVGERVTLTC<u>KASENVVTYVSW</u>YQQKPEQ
    SPKLLIY<u>GASNRYT</u>GVPDRFTGSGSATDFTLTISSVQAEDLADYHC<u>GQGYSYPYT</u>FGGGTKLEI
    K (SEQ ID: 71) (without leader sequence SEQ ID NO. 14)
- Light Chain 3 DNA Sequence
  - ATGAGGACCCCTGCTCAGTTTCTTGGAATCTTGTTGCTCTGGTTTCCAGGTATCAAATGTG
    ACATCAAGATGACCCAGTCTCCATCTTCCATGTATGCATCTCTAGGAGAGAGAGTCTGTAT
    CACTTGC<u>AAGGCGAGTCAGGACATTAATAGGTATTTAAGC</u>TGGATCCAGCAGAAACCAGG
    AAAAATCTCCTAAGACCCTGATCTAT<u>CGTACAGACAGATTGGTAGAG</u>GGGGCCCCATCAAG
    GTTCAGTGGCAGTGGATCTGCAACAGATTTCACTCTGACCATCAGCAGTGTGCAGGCTGA
    AGACCTTGCAGATTATCACTGT<u>GGACAGGGTTACAGCTATCCGTACACG</u>TTCGGAGGGGG
    GACCAAGCTGGAAATAAAA (SEQ ID: 72) (without leader sequence SEQ ID NO. 17)
- Light Chain 3 AA Seq
  - MRTPAQFLGILLLWFPGIKCDIKMTQSPSSMYASLGERVCITC<u>KASQDINRYLSW</u>IQQKPGKSP
    KTLIY<u>RTDRL</u>VEGAPSRFSGSGSATDFTLTISSVQAEDLADYHC<u>GQGYSYPYT</u>FGGGTKLEIK
    (SEQ ID: 73) (without leader sequence SEQ ID NO. 13)

FIG. 9

SEQUENCE LISTING

```
<160> NUMBER OF SEQ ID NOS: 79

<210> SEQ ID NO 1
<211> LENGTH: 132
<212> TYPE: PRT
<213> ORGANISM: Artificial
<220> FEATURE:
<223> OTHER INFORMATION: Synthetic

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Ser Tyr Thr Phe Tyr Pro Glu Ser Val
    50                  55                  60

Lys Gly Arg Ile Thr Val Tyr Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95
```

-continued

Ala Thr Leu His Tyr Asn Tyr Glu Arg Gly Ala Val Asp Tyr Trp Gly
            100                 105                 110

Gln Gly Thr Ser Val Thr Val Ser Ser Ala Thr Thr Thr Ala Pro Ser
        115                 120                 125

Val Tyr Pro Leu
        130

<210> SEQ ID NO 2
<211> LENGTH: 114
<212> TYPE: PRT
<213> ORGANISM: Artificial
<220> FEATURE:
<223> OTHER INFORMATION: Synthetic

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ala Met His Trp Val Lys Gln Ala Pro Ala Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Gly Asp Pro Leu Asp Tyr Trp Gly Gln Gly Thr Thr Leu Thr Val
            100                 105                 110

Ser Ser

<210> SEQ ID NO 3
<211> LENGTH: 114
<212> TYPE: PRT
<213> ORGANISM: Artificial
<220> FEATURE:
<223> OTHER INFORMATION: Synthetic

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ala Met His Trp Val Lys Gln Ala Pro Ala Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Gly Asp Pro Leu Asp Tyr Trp Gly Gln Gly Thr Thr Leu Thr Val
            100                 105                 110

Ser Ser

<210> SEQ ID NO 4
<211> LENGTH: 114
<212> TYPE: PRT

```
<213> ORGANISM: Artificial
<220> FEATURE:
<223> OTHER INFORMATION: Synthetic

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Phe
            20                  25                  30

Ala Met His Trp Val Lys Gln Ala Pro Arg Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Gly Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ser Ser Asp Pro Leu Asp Tyr Trp Gly Gln Gly Thr Thr Leu Thr Val
            100                 105                 110

Ser Ser

<210> SEQ ID NO 5
<211> LENGTH: 122
<212> TYPE: PRT
<213> ORGANISM: Artificial
<220> FEATURE:
<223> OTHER INFORMATION: Synthetic

<400> SEQUENCE: 5

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asn Met Gly Val Val Trp Ile Arg Gln Ser Ser Gly Lys Gly Leu Glu
        35                  40                  45

Trp Leu Leu His Ile Leu Trp Asn Asp Gly Lys Phe Tyr Asn Pro Ala
    50                  55                  60

Leu Lys Ser Arg Leu Thr Ile Ser Lys Asp Thr Tyr Asn Asn Gln Val
65                  70                  75                  80

Phe Leu Lys Ile Ala Asn Val Asp Thr Ala Asp Ala Thr Tyr Tyr Tyr
                85                  90                  95

Cys Ala Arg Leu Phe Ser Thr Thr Ser Gly Tyr Phe Asp Val Trp
            100                 105                 110

Gly Ala Gly Thr Thr Val Thr Val Ser Ser
        115                 120

<210> SEQ ID NO 6
<211> LENGTH: 122
<212> TYPE: PRT
<213> ORGANISM: Artificial
<220> FEATURE:
<223> OTHER INFORMATION: Synthetic

<400> SEQUENCE: 6

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30
```

```
Asn Met Gly Val Val Trp Ile Arg Gln Pro Ser Gly Lys Gly Leu Glu
            35                  40                  45

Trp Leu Leu His Ile Leu Trp Asn Asp Gly Lys Phe Tyr Asn Pro Ala
 50                  55                  60

Leu Lys Ser Arg Leu Thr Ile Ser Lys Asp Thr Tyr Asn Asn Gln Val
 65                  70                  75                  80

Phe Leu Lys Ile Ala Asn Val Asp Thr Ala Asp Thr Ala Thr Tyr Tyr
                 85                  90                  95

Cys Ala Arg Leu Phe Thr Thr Thr Thr Ser Gly Tyr Phe Asp Val Trp
                100                 105                 110

Gly Ala Gly Thr Thr Val Thr Val Ser Ser
            115                 120
```

<210> SEQ ID NO 7
<211> LENGTH: 121
<212> TYPE: PRT
<213> ORGANISM: Artificial
<220> FEATURE:
<223> OTHER INFORMATION: Synthetic

<400> SEQUENCE: 7

```
Asp Val Val Thr Gln Thr Pro Ser Ser Met Tyr Ala Ser Leu Gly
 1               5                  10                  15

Glu Arg Val Ser Ile Thr Cys Lys Ala Ser Gln Asp Ile Asn Arg Tyr
                 20                  25                  30

Leu Ser Trp Ile Gln Gln Lys Pro Gly Lys Ser Pro Lys Thr Leu Ile
             35                  40                  45

Tyr Arg Thr Asp Arg Leu Val Glu Gly Ala Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Asn Cys Leu Gln Tyr Asp Glu Phe Pro Val
                 85                  90                  95

Thr Phe Gly Ala Gly Thr Lys Leu Glu Ile Lys Arg Lys Ser Thr Ala
                100                 105                 110

Pro Thr Val Ser Lys Gly Glu Phe Val
            115                 120
```

<210> SEQ ID NO 8
<211> LENGTH: 112
<212> TYPE: PRT
<213> ORGANISM: Artificial
<220> FEATURE:
<223> OTHER INFORMATION: Synthetic

<400> SEQUENCE: 8

```
Asp Val Val Thr Gln Thr Pro Leu Ser Leu Pro Val Ser Phe Gly
 1               5                  10                  15

Asp Gln Val Ser Ile Ser Cys Arg Ser Ser Gln Ser Leu Ala Asn Ser
                 20                  25                  30

Tyr Gly Asn Thr Tyr Leu Ser Trp Tyr Leu His Lys Pro Gly Gln Ser
             35                  40                  45

Pro Gln Leu Leu Ile Tyr Glu Ile Ser Asn Arg Phe Ser Gly Val Ser
 50                  55                  60

Asp Arg Phe Ser Gly Ser Gly Ser Gly Thr Asp Phe Thr Leu Lys Ile
 65                  70                  75                  80

Ser Thr Ile Lys Pro Glu Asp Leu Gly Ile Tyr Tyr Cys Leu Gln Gly
                 85                  90                  95
```

Thr His Gln Pro Trp Thr Phe Gly Gly Gly Thr Lys Leu Glu Ile Lys
            100                 105                 110

<210> SEQ ID NO 9
<211> LENGTH: 112
<212> TYPE: PRT
<213> ORGANISM: Artificial
<220> FEATURE:
<223> OTHER INFORMATION: Synthetic

<400> SEQUENCE: 9

Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
                20                  25                  30

Tyr Gly Asn Thr Tyr Leu Ser Trp Tyr Leu His Lys Pro Gly Gln Ser
            35                  40                  45

Pro Gln Leu Leu Ile Tyr Glu Ile Ser Asn Arg Phe Ser Gly Val Ser
        50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Ile Tyr Tyr Cys Leu Gln Gly
                85                  90                  95

Thr His Gln Pro Trp Thr Phe Gly Gly Gly Thr Lys Leu Glu Ile Lys
            100                 105                 110

<210> SEQ ID NO 10
<211> LENGTH: 112
<212> TYPE: PRT
<213> ORGANISM: Artificial
<220> FEATURE:
<223> OTHER INFORMATION: Synthetic

<400> SEQUENCE: 10

Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Thr Asn Ser
                20                  25                  30

Tyr Gly Asn Thr Tyr Leu Ser Trp Phe Leu His Lys Pro Gly Gln Ser
            35                  40                  45

Pro Gln Leu Leu Ile Tyr Glu Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Ile Tyr Tyr Cys Leu Gln Gly
                85                  90                  95

Thr His Gln Pro Trp Thr Phe Gly Gly Gly Thr Lys Leu Glu Ile Lys
            100                 105                 110

<210> SEQ ID NO 11
<211> LENGTH: 107
<212> TYPE: PRT
<213> ORGANISM: Artificial
<220> FEATURE:
<223> OTHER INFORMATION: Synthetic

<400> SEQUENCE: 11

Asp Ile Gln Met Thr Gln Ser Pro Ala Ser Leu Ser Ala Ser Val Gly
1               5                   10                  15

```
Glu Thr Val Thr Ile Thr Cys Arg Ala Ser Gly Asn Ile His Asn Tyr
             20                  25                  30

Leu Ala Trp Tyr Gln Gln Lys Gln Gly Lys Ser Pro Gln Leu Leu Val
         35                  40                  45

Tyr Asn Ala Glu Thr Leu Ala Asp Gly Val Pro Ser Arg Phe Ser Gly
 50                  55                  60

Ser Glu Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Asp Thr Pro Trp
             85                  90                  95

Thr Phe Gly Gly Gly Thr Lys Leu Glu Ile Lys
            100                 105
```

```
<210> SEQ ID NO 12
<211> LENGTH: 107
<212> TYPE: PRT
<213> ORGANISM: Artificial
<220> FEATURE:
<223> OTHER INFORMATION: Synthetic

<400> SEQUENCE: 12

Asp Ile Gln Met Thr Gln Ser Pro Ala Ser Leu Ser Ala Ser Val Gly
1                5                  10                  15

Glu Thr Val Thr Ile Thr Cys Arg Ala Ser Gly Asn Ile Tyr Asn Tyr
             20                  25                  30

Leu Ala Trp Tyr Gln Gln Lys Gln Gly Lys Ser Pro Gln Leu Leu Val
         35                  40                  45

Tyr Asn Ala Lys Thr Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
65                  70                  75                  80

Glu Asp Phe Gly Ser Tyr Phe Cys Gln His Phe Trp Asp Thr Pro Trp
             85                  90                  95

Thr Phe Gly Gly Gly Thr Lys Leu Glu Ile Lys
            100                 105
```

```
<210> SEQ ID NO 13
<211> LENGTH: 107
<212> TYPE: PRT
<213> ORGANISM: Artificial
<220> FEATURE:
<223> OTHER INFORMATION: Synthetic

<400> SEQUENCE: 13

Asp Ile Lys Met Thr Gln Ser Pro Ser Ser Met Tyr Ala Ser Leu Gly
1                5                  10                  15

Glu Arg Val Cys Ile Thr Cys Lys Ala Ser Gln Asp Ile Asn Arg Tyr
             20                  25                  30

Leu Ser Trp Ile Gln Gln Lys Pro Gly Lys Ser Pro Lys Thr Leu Ile
         35                  40                  45

Tyr Arg Thr Asp Arg Leu Val Glu Gly Ala Pro Ser Arg Phe Ser Gly
 50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
             85                  90                  95

Thr Phe Gly Gly Gly Thr Lys Leu Glu Ile Lys
            100                 105
```

<210> SEQ ID NO 14
<211> LENGTH: 107
<212> TYPE: PRT
<213> ORGANISM: Artificial
<220> FEATURE:
<223> OTHER INFORMATION: Synthetic

<400> SEQUENCE: 14

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 15
<211> LENGTH: 107
<212> TYPE: PRT
<213> ORGANISM: Artificial
<220> FEATURE:
<223> OTHER INFORMATION: Synthetic

<400> SEQUENCE: 15

Asp Ile Lys Met Thr Gln Ser Pro Ser Ser Met Tyr Ala Ser Leu Gly
1               5                   10                  15

Glu Arg Val Ser Ile Thr Cys Lys Ala Ser Gln Asp Ile Asn Arg Tyr
            20                  25                  30

Leu Ser Trp Ile Gln Gln Lys Pro Gly Lys Ser Pro Lys Thr Leu Ile
        35                  40                  45

Tyr Arg Thr Asp Arg Leu Val Glu Gly Ala Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Asn Cys Leu Gln Tyr Asp Glu Phe Pro Val
                85                  90                  95

Thr Phe Gly Ala Gly Thr Lys Leu Glu Leu Lys
            100                 105

<210> SEQ ID NO 16
<211> LENGTH: 121
<212> TYPE: PRT
<213> ORGANISM: Artificial
<220> FEATURE:
<223> OTHER INFORMATION: Synthetic

<400> SEQUENCE: 16

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
            35                  40                  45

Ala Thr Ile Ser Ser Gly Gly Ser Tyr Thr Phe Tyr Pro Glu Ser Val
     50                  55                  60

Lys Gly Arg Ile Thr Val Tyr Arg Asp Asn Ala Arg Asn Thr Leu Tyr
 65                  70                  75                  80

Leu Gln Met Ser Ser Leu Arg Ser Glu Asp Thr Ala Leu Tyr Tyr Cys
                 85                  90                  95

Ala Thr Leu His Tyr Asn Tyr Glu Arg Gly Ala Val Asp Tyr Trp Gly
            100                 105                 110

Gln Gly Thr Ser Val Thr Val Ser Ser
        115                 120

<210> SEQ ID NO 17
<211> LENGTH: 321
<212> TYPE: DNA
<213> ORGANISM: Artificial
<220> FEATURE:
<223> OTHER INFORMATION: Synthetic

<400> SEQUENCE: 17
gacatcaaga tgacccagtc tccatcttcc atgtatgcat ctctaggaga gagagtctgt      60
atcacttgca aggcgagtca ggacattaat aggtatttaa gctggatcca gcagaaacca     120
ggaaaatctc ctaagaccct gatctatcgt acagacagat tggtagaggg ggccccatca     180
aggttcagtg gcagtggatc tgcaacagat tcactctga ccatcagcag tgtgcaggct      240
gaagaccttg cagattatca ctgtggacag ggttacagct atccgtacac gttcggaggg     300
gggaccaagc tggaaataaa a                                               321

<210> SEQ ID NO 18
<211> LENGTH: 9
<212> TYPE: PRT
<213> ORGANISM: Artificial
<220> FEATURE:
<223> OTHER INFORMATION: Synthetic

<400> SEQUENCE: 18

Phe Ala Phe Ser Ser Tyr Asp Met Ser
 1               5

<210> SEQ ID NO 19
<211> LENGTH: 10
<212> TYPE: PRT
<213> ORGANISM: Artificial
<220> FEATURE:
<223> OTHER INFORMATION: Synthetic

<400> SEQUENCE: 19

Gly Tyr Thr Phe Thr Asp Tyr Ala Met His
 1               5                  10

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Gly Tyr Thr Phe Thr Asp Phe Ala Met His
 1               5                  10

<210> SEQ ID NO 21
<211> LENGTH: 7
<212> TYPE: PRT
<213> ORGANISM: Artificial
<220> FEATURE:
<223> OTHER INFORMATION: Synthetic

<400> SEQUENCE: 21

Thr Ser Asn Met Gly Val Val
1               5

<210> SEQ ID NO 22
<211> LENGTH: 17
<212> TYPE: PRT
<213> ORGANISM: Artificial
<220> FEATURE:
<223> OTHER INFORMATION: Synthetic

<400> SEQUENCE: 22

Thr Ile Ser Ser Gly Gly Ser Tyr Thr Phe Tyr Pro Glu Ser Val Lys
1               5                   10                  15

Gly

<210> SEQ ID NO 23
<211> LENGTH: 17
<212> TYPE: PRT
<213> ORGANISM: Artificial
<220> FEATURE:
<223> OTHER INFORMATION: Synthetic

<400> SEQUENCE: 23

Trp Ile Asn Thr Glu Thr Gly Glu Pro Thr Tyr Ala Asp Asp Phe Lys
1               5                   10                  15

Gly

<210> SEQ ID NO 24
<211> LENGTH: 16
<212> TYPE: PRT
<213> ORGANISM: Artificial
<220> FEATURE:
<223> OTHER INFORMATION: Synthetic

<400> SEQUENCE: 24

His Ile Leu Trp Asn Asp Gly Lys Phe Tyr Asn Pro Ala Leu Lys Ser
1               5                   10                  15

<210> SEQ ID NO 25
<211> LENGTH: 12
<212> TYPE: PRT
<213> ORGANISM: Artificial
<220> FEATURE:
<223> OTHER INFORMATION: Synthetic

<400> SEQUENCE: 25

Leu His Tyr Asn Tyr Glu Arg Gly Ala Val Asp Tyr
1               5                   10

<210> SEQ ID NO 26
<211> LENGTH: 5
<212> TYPE: PRT
<213> ORGANISM: Artificial
<220> FEATURE:
<223> OTHER INFORMATION: Synthetic

<400> SEQUENCE: 26

```
Asp Pro Leu Asp Tyr
1               5
```

<210> SEQ ID NO 27
<211> LENGTH: 12
<212> TYPE: PRT
<213> ORGANISM: Artificial
<220> FEATURE:
<223> OTHER INFORMATION: Synthetic

<400> SEQUENCE: 27

```
Leu Phe Ser Thr Thr Thr Ser Gly Tyr Phe Asp Val
1               5                   10
```

<210> SEQ ID NO 28
<211> LENGTH: 12
<212> TYPE: PRT
<213> ORGANISM: Artificial
<220> FEATURE:
<223> OTHER INFORMATION: Synthetic

<400> SEQUENCE: 28

```
Leu Phe Thr Thr Thr Thr Ser Gly Tyr Phe Asp Val
1               5                   10
```

<210> SEQ ID NO 29
<211> LENGTH: 11
<212> TYPE: PRT
<213> ORGANISM: Artificial
<220> FEATURE:
<223> OTHER INFORMATION: Synthetic

<400> SEQUENCE: 29

```
Lys Ala Ser Gln Asp Ile Asn Arg Tyr Leu Ser
1               5                   10
```

<210> SEQ ID NO 30
<211> LENGTH: 11
<212> TYPE: PRT
<213> ORGANISM: Artificial
<220> FEATURE:
<223> OTHER INFORMATION: Synthetic

<400> SEQUENCE: 30

```
Lys Ala Ser Glu Asn Val Val Thr Tyr Val Ser
1               5                   10
```

<210> SEQ ID NO 31
<211> LENGTH: 16
<212> TYPE: PRT
<213> ORGANISM: Artificial
<220> FEATURE:
<223> OTHER INFORMATION: Synthetic

<400> SEQUENCE: 31

```
Arg Ser Ser Gln Ser Leu Ala Asn Ser Tyr Gly Asn Thr Tyr Leu Ser
1               5                   10                  15
```

<210> SEQ ID NO 32
<211> LENGTH: 16
<212> TYPE: PRT
<213> ORGANISM: Artificial
<220> FEATURE:
<223> OTHER INFORMATION: Synthetic

<400> SEQUENCE: 32

```
Arg Ser Ser Gln Ser Leu Thr Asn Ser Tyr Gly Asn Thr Tyr Leu Ser
```

```
<210> SEQ ID NO 33
<211> LENGTH: 11
<212> TYPE: PRT
<213> ORGANISM: Artificial
<220> FEATURE:
<223> OTHER INFORMATION: Synthetic

<400> SEQUENCE: 33

Arg Ala Ser Gly Asn Ile His Asn Tyr Leu Ala
1               5                   10

<210> SEQ ID NO 34
<211> LENGTH: 11
<212> TYPE: PRT
<213> ORGANISM: Artificial
<220> FEATURE:
<223> OTHER INFORMATION: Synthetic

<400> SEQUENCE: 34

Arg Ala Ser Gly Asn Ile Tyr Asn Tyr Leu Ala
1               5                   10

<210> SEQ ID NO 35
<211> LENGTH: 7
<212> TYPE: PRT
<213> ORGANISM: Artificial
<220> FEATURE:
<223> OTHER INFORMATION: Synthetic

<400> SEQUENCE: 35

Arg Thr Asp Arg Leu Val Glu
1               5

<210> SEQ ID NO 36
<211> LENGTH: 7
<212> TYPE: PRT
<213> ORGANISM: Artificial
<220> FEATURE:
<223> OTHER INFORMATION: Synthetic

<400> SEQUENCE: 36

Gly Ala Ser Asn Arg Tyr Thr
1               5

<210> SEQ ID NO 37
<211> LENGTH: 7
<212> TYPE: PRT
<213> ORGANISM: Artificial
<220> FEATURE:
<223> OTHER INFORMATION: Synthetic

<400> SEQUENCE: 37

Glu Ile Ser Asn Arg Phe Ser
1               5

<210> SEQ ID NO 38
<211> LENGTH: 7
<212> TYPE: PRT
<213> ORGANISM: Artificial
<220> FEATURE:
<223> OTHER INFORMATION: Synthetic

<400> SEQUENCE: 38

Asn Ala Glu Thr Leu Ala Asp
1               5
```

```
<210> SEQ ID NO 39
<211> LENGTH: 7
<212> TYPE: PRT
<213> ORGANISM: Artificial
<220> FEATURE:
<223> OTHER INFORMATION: Synthetic

<400> SEQUENCE: 39

Asn Ala Lys Thr Leu Ala Asp
1               5

<210> SEQ ID NO 40
<211> LENGTH: 9
<212> TYPE: PRT
<213> ORGANISM: Artificial
<220> FEATURE:
<223> OTHER INFORMATION: Synthetic

<400> SEQUENCE: 40

Leu Gln Tyr Asp Glu Phe Pro Val Thr
1               5

<210> SEQ ID NO 41
<211> LENGTH: 9
<212> TYPE: PRT
<213> ORGANISM: Artificial
<220> FEATURE:
<223> OTHER INFORMATION: Synthetic

<400> SEQUENCE: 41

Leu Gln Gly Thr His Gln Pro Trp Thr
1               5

<210> SEQ ID NO 42
<211> LENGTH: 9
<212> TYPE: PRT
<213> ORGANISM: Artificial
<220> FEATURE:
<223> OTHER INFORMATION: Synthetic

<400> SEQUENCE: 42

Gln His Phe Trp Asp Thr Pro Trp Thr
1               5

<210> SEQ ID NO 43
<211> LENGTH: 9
<212> TYPE: PRT
<213> ORGANISM: Artificial
<220> FEATURE:
<223> OTHER INFORMATION: Synthetic

<400> SEQUENCE: 43

Gly Gln Gly Tyr Ser Tyr Pro Tyr Thr
1               5

<210> SEQ ID NO 44
<211> LENGTH: 342
<212> TYPE: DNA
<213> ORGANISM: Artificial
<220> FEATURE:
<223> OTHER INFORMATION: Synthetic

<400> SEQUENCE: 44
cagatccagt tggtgcagtc tggacctgag ctgaagaagc tggagagaca agtcaagatc      60
tcctgcaagg cttctggtta taccttcaca gactatgcaa tgcactgggt gaagcaggct     120
```

```
ccagcaaagg gtttaaagtg gatgggctgg ataaacactg agactggtga gccaacatat    180
gcagatgact tcaagggacg gtttgccttc tctttggaaa cctctgccag cactgcctat    240
ttacagatca caacctcaa aaatgaggac acggcaacat atttctgtgc tggcgaccct    300
cttgactact ggggccaggg caccactctc acagtctcct ca                      342
```

<210> SEQ ID NO 45
<211> LENGTH: 336
<212> TYPE: DNA
<213> ORGANISM: Artificial
<220> FEATURE:
<223> OTHER INFORMATION: Synthetic

<400> SEQUENCE: 45

```
gatgttgtgg tgactcaaac tccactctcc ctgcctgtca gctttggaga tcaagtttct     60
atctcttgca ggtctagtca gagtcttgca acagttatg gaacaccta tttgtcttgg    120 tacctacaca gcctggcca gtctccacag ctcctcatct atgagatttc caacagattt    180
tctggggtgt cagacaggtt cagtggcagt ggttcaggga cagatttcac actcaagatc    240
agcacaataa agcctgagga cttgggaata tattactgct acaaggtac acatcagccg    300 tggacgttcg gtggaggcac caagctggaa atcaaa                              336
```

<210> SEQ ID NO 46
<211> LENGTH: 321
<212> TYPE: DNA
<213> ORGANISM: Artificial
<220> FEATURE:
<223> OTHER INFORMATION: Synthetic

<400> SEQUENCE: 46

```
aacattgtaa tgacccaatc tcccaaatcc atgtccatgt cagtaggaga gagggtcacc     60
ttgacctgca aggccagtga aaatgtggtt acttatgttt cctggtatca acagaaacca    120
gagcagtctc ctaaactgct gatatacggg gcatccaacc ggtacactgg ggtccccgat    180
cgcttcacag gcagtggatc tgcaacagat ttcactctga ccatcagcag tgtgcaggct    240
gaagaccttg cagattatca ctgtggacag ggttacagct atccgtacac gttcggaggg    300
gggaccaagc tggaaataaa a                                              321
```

<210> SEQ ID NO 47
<211> LENGTH: 107
<212> TYPE: PRT
<213> ORGANISM: Artificial
<220> FEATURE:
<223> OTHER INFORMATION: Synthetic

<400> SEQUENCE: 47

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
```

```
                85                  90                  95
Thr Phe Gly Gly Gly Thr Lys Leu Glu Ile Lys
            100                 105

<210> SEQ ID NO 48
<211> LENGTH: 363
<212> TYPE: DNA
<213> ORGANISM: Artificial
<220> FEATURE:
<223> OTHER INFORMATION: Synthetic

<400> SEQUENCE: 48
gaagtgaagc tggtggagtc aggggggaggc ttagtgaagc tggagggtc cctgaaactc      60 tcctgtgcag cctctggatt cgccttcagt agctatgaca tgtcttgggt tcgccagact     120
ccggagaaga ggctggagtg gtcgcaacc attagtagtg gtggtagtta caccttctat     180
ccagaaagtg tgaagggccg aatcaccgtc tacagagaca tgccaggaa cacctgtac      240 ctgcaaatga gcagtctgcg gtctgaggac acggccttgt attactgtgc aaccctccat     300
tataattacg agaggggtgc tgtggactac tggggtcaag aaccctcagt caccgtctcc     360
tca                                                                   363

<210> SEQ ID NO 49
<211> LENGTH: 321
<212> TYPE: DNA
<213> ORGANISM: Artificial
<220> FEATURE:
<223> OTHER INFORMATION: Synthetic

<400> SEQUENCE: 49
gacatcaaga tgacccagtc tccatcttcc atgtatgcat ctctaggaga gagagtcagt      60
atcacttgca aggcgagtca ggacattaat aggtatttaa gctggatcca gcagaaacca     120
ggaaaatctc ctaagaccct gatctatcgt acagacagat ggtagaggg ggccccatca      180 aggttcagtg gcagtggatc tgggcaagat tattctctca ccatcagcag cctggagtat     240
gaagatatgg gaatttataa ttgtctacag tatgatgagt ttccggtcac gttcggtgct     300
gggaccaagc tggagctgaa a                                               321

<210> SEQ ID NO 50
<211> LENGTH: 321
<212> TYPE: DNA
<213> ORGANISM: Artificial
<220> FEATURE:
<223> OTHER INFORMATION: Synthetic

<400> SEQUENCE: 50
aacattgtaa tgacccaatc tcccaaatcc atgtccatgt cagtaggaga gagggtcacc      60
ttgacctgca aggccagtga gaatgtggtt acttatgttt cctggtatca acagaaacca     120
gagcagtctc ctaaactgct gatatacggg gcatccaacc ggtacactgg ggtccccgat     180
cgcttcacag gcagtggatc tgcaacagat ttcactctga ccatcagcag tgtgcaggct     240
gaagaccttg cagattatca ctgtggacag ggttacagct atccgtacac gttcggaggg     300
gggaccaagc tggaaataaa a                                               321

<210> SEQ ID NO 51
<211> LENGTH: 4
<212> TYPE: PRT
<213> ORGANISM: Artificial
<220> FEATURE:
```

<223> OTHER INFORMATION: Synthetic
<220> FEATURE:
<221> NAME/KEY: X
<222> LOCATION: (1)..(4)
<223> OTHER INFORMATION: Wherein X is any amino acid

<400> SEQUENCE: 51

Phe Gly Xaa Gly
1

<210> SEQ ID NO 52
<211> LENGTH: 24
<212> TYPE: PRT
<213> ORGANISM: Artificial
<220> FEATURE:
<223> OTHER INFORMATION: Synthetic

<400> SEQUENCE: 52

Glu Leu Asp Gln Pro Pro Lys Leu Arg Gly Val Leu Gln Gly His Leu
1               5                   10                  15

Glu Ser Ser Arg Asn Asp Pro Phe
            20

<210> SEQ ID NO 53
<211> LENGTH: 10
<212> TYPE: PRT
<213> ORGANISM: Artificial
<220> FEATURE:
<223> OTHER INFORMATION: Synthetic

<400> SEQUENCE: 53

Lys Leu Arg Gly Val Leu Gln Gly His Leu
1               5                   10

<210> SEQ ID NO 54
<211> LENGTH: 140
<212> TYPE: PRT
<213> ORGANISM: Artificial
<220> FEATURE:
<223> OTHER INFORMATION: Synthetic

<400> SEQUENCE: 54

Ile Val Ile Arg Leu Thr Ile Gly Arg Ile Glu Phe Ser Gly Arg Glu
1               5                   10                  15

Phe Ala Leu Asp Val Val Val Thr Gln Thr Pro Ser Ser Met Tyr Ala
            20                  25                  30

Ser Leu Gly Glu Arg Val Ser Ile Thr Cys Lys Ala Ser Gln Asp Ile
        35                  40                  45

Asn Arg Tyr Leu Ser Trp Ile Gln Gln Lys Pro Gly Lys Ser Pro Lys
    50                  55                  60

Thr Leu Ile Tyr Arg Thr Asp Arg Leu Val Glu Gly Ala Pro Ser Arg
65                  70                  75                  80

Phe Ser Gly Ser Gly Ser Gly Gln Asp Tyr Ser Leu Thr Ile Ser Ser
                85                  90                  95

Leu Glu Tyr Glu Asp Met Gly Ile Tyr Asn Cys Leu Gln Tyr Asp Glu
            100                 105                 110

Phe Pro Val Thr Phe Gly Ala Gly Thr Lys Leu Glu Ile Lys Arg Lys
        115                 120                 125

Ser Thr Ala Pro Thr Val Ser Lys Gly Glu Phe Val
    130                 135                 140

<210> SEQ ID NO 55

<211> LENGTH: 132
<212> TYPE: PRT
<213> ORGANISM: Artificial
<220> FEATURE:
<223> OTHER INFORMATION: Synthetic

<400> SEQUENCE: 55

Met Asn Leu Pro Val His Leu Leu Val Leu Leu Phe Trp Ile Pro
1               5                   10                  15

Ala Ser Arg Gly Asp Val Val Thr Gln Thr Pro Leu Ser Leu Pro
            20                  25                  30

Val Ser Phe Gly Asp Gln Val Ser Ile Ser Cys Arg Ser Ser Gln Ser
        35                  40                  45

Leu Ala Asn Ser Tyr Gly Asn Thr Tyr Leu Ser Trp Tyr Leu His Lys
    50                  55                  60

Pro Gly Gln Ser Pro Gln Leu Leu Ile Tyr Glu Ile Ser Asn Arg Phe
65                  70                  75                  80

Ser Gly Val Ser Asp Arg Phe Ser Gly Ser Gly Ser Gly Thr Asp Phe
                85                  90                  95

Thr Leu Lys Ile Ser Thr Ile Lys Pro Glu Asp Leu Gly Ile Tyr Tyr
            100                 105                 110

Cys Leu Gln Gly Thr His Gln Pro Trp Thr Phe Gly Gly Gly Thr Lys
            115                 120                 125

Leu Glu Ile Lys
    130

<210> SEQ ID NO 56
<211> LENGTH: 132
<212> TYPE: PRT
<213> ORGANISM: Artificial
<220> FEATURE:
<223> OTHER INFORMATION: Synthetic

<400> SEQUENCE: 56

Met Asn Leu Pro Val His Leu Leu Val Leu Leu Phe Trp Ile Pro
1               5                   10                  15

Ala Ser Arg Gly Asp Val Val Thr Gln Thr Pro Leu Ser Leu Pro
            20                  25                  30

Val Ser Phe Gly Asp Gln Val Ser Ile Ser Cys Arg Ser Ser Gln Ser
        35                  40                  45

Leu Ala Asn Ser Tyr Gly Asn Thr Tyr Leu Ser Trp Tyr Leu His Lys
    50                  55                  60

Pro Gly Gln Ser Pro Gln Leu Leu Ile Tyr Glu Ile Ser Asn Arg Phe
65                  70                  75                  80

Ser Gly Val Ser Asp Arg Phe Ser Gly Ser Gly Ser Gly Thr Asp Phe
                85                  90                  95

Thr Leu Lys Ile Ser Thr Ile Lys Pro Glu Asp Leu Gly Ile Tyr Tyr
            100                 105                 110

Cys Leu Gln Gly Thr His Gln Pro Trp Thr Phe Gly Gly Gly Thr Lys
            115                 120                 125

Leu Glu Ile Lys
    130

<210> SEQ ID NO 57
<211> LENGTH: 132
<212> TYPE: PRT
<213> ORGANISM: Artificial
<220> FEATURE:
<223> OTHER INFORMATION: Synthetic -continued

<400> SEQUENCE: 57

Met Asn Leu Pro Val His Leu Leu Val Leu Leu Phe Trp Ile Pro
1               5                   10                  15

Ala Ser Arg Gly Asp Val Val Thr Gln Thr Pro Leu Ser Leu Pro
                20                  25                  30

Val Ser Phe Gly Asp Gln Val Ser Ile Ser Cys Arg Ser Gln Ser
            35                  40                  45

Leu Thr Asn Ser Tyr Gly Asn Thr Tyr Leu Ser Trp Phe Leu His Lys
        50                  55                  60

Pro Gly Gln Ser Pro Gln Leu Leu Ile Tyr Glu Ile Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Thr Ile Lys Pro Glu Asp Leu Gly Ile Tyr Tyr
            100                 105                 110

Cys Leu Gln Gly Thr His Gln Pro Trp Thr Phe Gly Gly Gly Thr Lys
        115                 120                 125

Leu Glu Ile Lys
    130

<210> SEQ ID NO 58
<211> LENGTH: 127
<212> TYPE: PRT
<213> ORGANISM: Artificial
<220> FEATURE:
<223> OTHER INFORMATION: Synthetic

<400> SEQUENCE: 58

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
            35                  40                  45

Ile His Asn Tyr Leu Ala Trp Tyr Gln Gln Lys Gln Gly Lys Ser Pro
        50                  55                  60

Gln Leu Leu Val Tyr Asn Ala Glu Thr Leu Ala Asp Gly Val Pro Ser
65                  70                  75                  80

Arg Phe Ser Gly Ser Glu Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Asp Thr Pro Trp Thr Phe Gly Gly Gly Thr Lys Leu Glu Ile Lys
        115                 120                 125

<210> SEQ ID NO 59
<211> LENGTH: 127
<212> TYPE: PRT
<213> ORGANISM: Artificial
<220> FEATURE:
<223> OTHER INFORMATION: Synthetic

<400> SEQUENCE: 59

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
            35                  40                  45

Ile Tyr Asn Tyr Leu Ala Trp Tyr Gln Gln Lys Gln Gly Lys Ser Pro
     50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Phe Cys Gln His Phe Trp
            100                 105                 110

Asp Thr Pro Trp Thr Phe Gly Gly Gly Thr Lys Leu Glu Ile Lys
        115                 120                 125

<210> SEQ ID NO 60
<211> LENGTH: 399
<212> TYPE: DNA
<213> ORGANISM: Artificial
<220> FEATURE:
<223> OTHER INFORMATION: Synthetic

<400> SEQUENCE: 60
atggcttggg tgtggacctt gctattcctg atggcagctg cccaaagtat ccaagcacag    60
atccagttgg tgcagtctgg acctgagctg aagaagcctg agagacagt caagatctcc    120 tgcaaggctt ctggttatac cttcacagac tatgcaatgc actgggtgaa gcaggctcca    180
gcaaagggtt taaagtggat gggctggata aacactgaga ctggtgagcc aacatatgca    240
gatgacttca agggacggtt tgccttctct ttggaaacct ctgccagcac tgcctattta    300
cagatcaaca acctcaaaaa tgaggacacg gcaacatatt tctgtgctgg cgaccctctt    360
gactactggg gccagggcac cactctcaca gtctcctca                           399

<210> SEQ ID NO 61
<211> LENGTH: 133
<212> TYPE: PRT
<213> ORGANISM: Artificial
<220> FEATURE:
<223> OTHER INFORMATION: Synthetic

<400> SEQUENCE: 61

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ala Met His Trp Val Lys Gln Ala Pro Ala Lys Gly Leu
     50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Gly Asp Pro Leu Asp Tyr Trp Gly Gln Gly Thr Thr
        115                 120                 125

Leu Thr Val Ser Ser
        130

<210> SEQ ID NO 62
<211> LENGTH: 396
<212> TYPE: DNA
<213> ORGANISM: Artificial
<220> FEATURE:
<223> OTHER INFORMATION: Synthetic

<400> SEQUENCE: 62

```
atgaatttgc ctgttcatct cttggtgctt ctgttgttct ggattcctgc ttccagaggt    60
gatgttgtgg tgactcaaac tccactctcc ctgcctgtca gctttggaga tcaagtttct   120
atctcttgca ggtctagtca gagtcttgca aacagttatg gaacaccta tttgtcttgg    180 tacctacaca agcctggcca gtctccacag ctcctcatct atgagatttc aacagattt    240 tctggggtgt cagacaggtt cagtggcagt ggttcaggga cagatttcac actcaagatc   300
agcacaataa agcctgagga cttgggaata tattactgct acaaggtac acatcagccg    360 tggacgttcg gtggaggcac caagctggaa atcaaa                              396
```

<210> SEQ ID NO 63
<211> LENGTH: 132
<212> TYPE: PRT
<213> ORGANISM: Artificial
<220> FEATURE:
<223> OTHER INFORMATION: Synthetic

<400> SEQUENCE: 63

```
Met Asn Leu Pro Val His Leu Leu Val Leu Leu Leu Phe Trp Ile Pro
1               5                   10                  15

Ala Ser Arg Gly Asp Val Val Thr Gln Thr Pro Leu Ser Leu Pro
            20                  25                  30

Val Ser Phe Gly Asp Gln Val Ser Ile Ser Cys Arg Ser Ser Gln Ser
        35                  40                  45

Leu Ala Asn Ser Tyr Gly Asn Thr Tyr Leu Ser Trp Tyr Leu His Lys
    50                  55                  60

Pro Gly Gln Ser Pro Gln Leu Leu Ile Tyr Glu Ile Ser Asn Arg Phe
65                  70                  75                  80

Ser Gly Val Ser Asp Arg Phe Ser Gly Ser Gly Ser Gly Thr Asp Phe
                85                  90                  95

Thr Leu Lys Ile Ser Thr Ile Lys Pro Glu Asp Leu Gly Ile Tyr Tyr
            100                 105                 110

Cys Leu Gln Gly Thr His Gln Pro Trp Thr Phe Gly Gly Gly Thr Lys
        115                 120                 125

Leu Glu Ile Lys
    130
```

<210> SEQ ID NO 64
<211> LENGTH: 381
<212> TYPE: DNA
<213> ORGANISM: Artificial
<220> FEATURE:
<223> OTHER INFORMATION: Synthetic

<400> SEQUENCE: 64

```
atggaatcac agactctggt cttcatatcc atactgctct ggttatatgg agctgatggg    60
aacattgtaa tgacccaatc tcccaaatcc atgtccatgt cagtaggaga gagggtcacc   120
ttgacctgca aggccagtga gaatgtggtt acttatgttt cctggtatca acagaaacca   180
gagcagtctc ctaaactgct gatatacggg gcatccaacc ggtacactgg ggtccccgat   240
```

```
cgcttcacag gcagtggatc tgcaacagat tcactctga ccatcagcag tgtgcaggct    300
gaagaccttg cagattatca ctgtggacag ggttacagct atccgtacac gttcggaggg    360
gggaccaagc tggaaataaa a                                              381
```

<210> SEQ ID NO 65
<211> LENGTH: 127
<212> TYPE: PRT
<213> ORGANISM: Artificial
<220> FEATURE:
<223> OTHER INFORMATION: Synthetic

<400> SEQUENCE: 65

```
Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys
        115                 120                 125
```

<210> SEQ ID NO 66
<211> LENGTH: 420
<212> TYPE: DNA
<213> ORGANISM: Artificial
<220> FEATURE:
<223> OTHER INFORMATION: Synthetic

<400> SEQUENCE: 66

```
atgaactttg ggctgagctt gattttcctt gtcctaattt taaaaggtgt ccagtgtgaa    60
gtgaagctgg tggagtcagg gggaggctta gtgaagcctg agggtccct gaaactctcc    120 tgtgcagcct ctggattcgc cttcagtagc tatgacatgt cttgggttcg ccagactccg    180
gagaagaggc tggagtgggt cgcaaccatt agtagtggtg gtagttacac cttctatcca    240
gaaagtgtga agggccgaat caccgtctac agagacaatg ccaggaacac cctgtacctg    300
caaatgagca gtctgcggtc tgaggacacg gccttgtatt actgtgcaac cctccattat    360
aattacgaga ggggtgctgt ggactactgg ggtcaaggaa cctcagtcac cgtctcctca    420
```

<210> SEQ ID NO 67
<211> LENGTH: 140
<212> TYPE: PRT
<213> ORGANISM: Artificial
<220> FEATURE:
<223> OTHER INFORMATION: Synthetic

<400> SEQUENCE: 67

```
Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Gly Leu Val Lys
```

20                  25                  30
Pro Gly Gly Ser Leu Lys Leu Ser Cys Ala Ala Ser Gly Phe Ala Phe
                35                  40                  45

Ser Ser Tyr Asp Met Ser Trp Val Arg Gln Thr Pro Glu Lys Arg Leu
    50                  55                  60

Glu Trp Val Ala Thr Ile Ser Ser Gly Gly Ser Tyr Thr Phe Tyr Pro
65                  70                  75                  80

Glu Ser Val Lys Gly Arg Ile Thr Val Tyr Arg Asp Asn Ala Arg Asn
                85                  90                  95

Thr Leu Tyr Leu Gln Met Ser Ser Leu Arg Ser Glu Asp Thr Ala Leu
            100                 105                 110

Tyr Tyr Cys Ala Thr Leu His Tyr Asn Tyr Glu Arg Gly Ala Val Asp
        115                 120                 125

Tyr Trp Gly Gln Gly Thr Ser Val Thr Val Ser Ser
    130                 135                 140

<210> SEQ ID NO 68
<211> LENGTH: 381
<212> TYPE: DNA
<213> ORGANISM: Artificial
<220> FEATURE:
<223> OTHER INFORMATION: Synthetic

<400> SEQUENCE: 68
atgaggaccc ctgctcagtt tcttggaatc ttgttgctct ggtttccagg tatcaaatgt      60
gacatcaaga tgacccagtc tccatcttcc atgtatgcat ctctaggaga gagagtcagt     120
atcacttgca aggcgagtca ggacattaat aggtatttaa gctggatcca gcagaaacca     180
ggaaaatctc ctaagaccct gatctatcgt acagacagat tggtagaggg ggcccccatca    240 aggttcagtg gcagtggatc tgggcaagat tattctctca ccatcagcag cctggagtat     300
gaagatatgg gaatttataa ttgtctacag tatgatgagt ttccggtcac gttcggtgct     360
gggaccaagc tggagctgaa a                                                381

<210> SEQ ID NO 69
<211> LENGTH: 127
<212> TYPE: PRT
<213> ORGANISM: Artificial
<220> FEATURE:
<223> OTHER INFORMATION: Synthetic

<400> SEQUENCE: 69

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Ser Ile Thr Cys Lys Ala Ser Gln Asp
        35                  40                  45

Ile Asn Arg Tyr Leu Ser Trp Ile Gln Gln Lys Pro Gly Lys Ser Pro
    50                  55                  60

Lys Thr Leu Ile Tyr Arg Thr Asp Arg Leu Val Glu Gly Ala Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Ile Tyr Asn Cys Leu Gln Tyr Asp
            100                 105                 110

Glu Phe Pro Val Thr Phe Gly Ala Gly Thr Lys Leu Glu Leu Lys

<210> SEQ ID NO 70
<211> LENGTH: 381
<212> TYPE: DNA
<213> ORGANISM: Artificial
<220> FEATURE:
<223> OTHER INFORMATION: Synthetic

<400> SEQUENCE: 70

```
atggaatcac agactctggt cttcatatcc atactgctct ggttatatgg agctgatggg      60
aacattgtaa tgacccaatc tcccaaatcc atgtccatgt cagtaggaga gagggtcacc     120
ttgacctgca aggccagtga aaatgtggtt acttatgttt cctggtatca acagaaacca     180
gagcagtctc ctaaactgct gatatacggg gcatccaacc ggtacactgg ggtcccgat      240
cgcttcacag gcagtggatc tgcaacagat ttcactctga ccatcagcag tgtgcaggct     300
gaagaccttg cagattatca ctgtggacag ggttacagct atccgtacac gttcggaggg     360
gggaccaagc tggaaataaa a                                                381
```

<210> SEQ ID NO 71
<211> LENGTH: 127
<212> TYPE: PRT
<213> ORGANISM: Artificial
<220> FEATURE:
<223> OTHER INFORMATION: Synthetic

<400> SEQUENCE: 71

Met Glu Ser Gln Thr Leu Val Phe Ile Ser Ile Leu Leu Trp Leu Tyr
1               5                   10                  15
Gly Ala Asp Gly Asn Ile Val Met Thr Gln Ser Pro Lys Ser Met Ser
            20                  25                  30
Met Ser Val Gly Glu Arg Val Thr Leu Thr Cys Lys Ala Ser Glu Asn
        35                  40                  45
Val Val Thr Tyr Val Ser Trp Tyr Gln Gln Lys Pro Glu Gln Ser Pro
    50                  55                  60
Lys Leu Leu Ile Tyr Gly Ala Ser Asn Arg Tyr Thr Gly Val Pro Asp
65                  70                  75                  80
Arg Phe Thr Gly Ser Gly Ser Ala Thr Asp Phe Thr Leu Thr Ile Ser
                85                  90                  95
Ser Val Gln Ala Glu Asp Leu Ala Asp Tyr His Cys Gly Gln Gly Tyr
            100                 105                 110
Ser Tyr Pro Tyr Thr Phe Gly Gly Gly Thr Lys Leu Glu Ile Lys
        115                 120                 125

<210> SEQ ID NO 72
<211> LENGTH: 381
<212> TYPE: DNA
<213> ORGANISM: Artificial
<220> FEATURE:
<223> OTHER INFORMATION: Synthetic

<400> SEQUENCE: 72

```
atgaggaccc ctgctcagtt tcttggaatc ttgttgctct ggtttccagg tatcaaatgt      60
gacatcaaga tgacccagtc tccatcttcc atgtatgcat ctctaggaga gagagtctgt     120
atcacttgca aggcgagtca ggacattaat aggtatttaa gctggatcca gcagaaacca     180
ggaaaatctc ctaagaccct gatctatcgt acagacagat ggtagaggg ggccccatca      240
aggttcagtg gcagtggatc tgcaacagat ttcactctga ccatcagcag tgtgcaggct     300
```

```
gaagaccttg cagattatca ctgtggacag ggttacagct atccgtacac gttcggaggg    360
gggaccaagc tggaaataaa a                                              381
```

<210> SEQ ID NO 73
<211> LENGTH: 127
<212> TYPE: PRT
<213> ORGANISM: Artificial
<220> FEATURE:
<223> OTHER INFORMATION: Synthetic

<400> SEQUENCE: 73

```
Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Cys Ile Thr Cys Lys Ala Ser Gln Asp
        35                  40                  45

Ile Asn Arg Tyr Leu Ser Trp Ile Gln Gln Lys Pro Gly Lys Ser Pro
    50                  55                  60

Lys Thr Leu Ile Tyr Arg Thr Asp Arg Leu Val Glu Gly Ala Pro Ser
65                  70                  75                  80

Arg Phe Ser Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys
        115                 120                 125
```

<210> SEQ ID NO 74
<211> LENGTH: 151
<212> TYPE: PRT
<213> ORGANISM: Artificial
<220> FEATURE:
<223> OTHER INFORMATION: Synthetic

<400> SEQUENCE: 74

```
Met Asp Phe Gly Leu Ser Leu Val Phe Leu Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Ser Tyr Asp Met Ser Trp Val Arg Gln Thr Pro Glu Lys Arg Leu
    50                  55                  60

Glu Trp Val Ala Thr Ile Ser Ser Gly Gly Ser Tyr Thr Phe Tyr Pro
65                  70                  75                  80

Glu Ser Val Lys Gly Arg Ile Thr Val Tyr Arg Asp Asn Ala Arg Asn
                85                  90                  95

Thr Leu Tyr Leu Gln Met Ser Ser Leu Arg Ser Glu Asp Thr Ala Leu
            100                 105                 110

Tyr Tyr Cys Ala Thr Leu His Tyr Asn Tyr Glu Arg Gly Ala Val Asp
        115                 120                 125

Tyr Trp Gly Gln Gly Thr Ser Val Thr Val Ser Ser Ala Thr Thr Thr
    130                 135                 140

Ala Pro Ser Val Tyr Pro Leu
145                 150
```

```
<210> SEQ ID NO 75
<211> LENGTH: 133
<212> TYPE: PRT
<213> ORGANISM: Artificial
<220> FEATURE:
<223> OTHER INFORMATION: Synthetic

<400> SEQUENCE: 75

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ala Met His Trp Val Lys Gln Ala Pro Ala Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Gly Asp Pro Leu Asp Tyr Trp Gly Gln Gly Thr Thr
        115                 120                 125

Leu Thr Val Ser Ser
    130

<210> SEQ ID NO 76
<211> LENGTH: 133
<212> TYPE: PRT
<213> ORGANISM: Artificial
<220> FEATURE:
<223> OTHER INFORMATION: Synthetic

<400> SEQUENCE: 76

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ala Met His Trp Val Lys Gln Ala Pro Ala Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Gly Asp Pro Leu Asp Tyr Trp Gly Gln Gly Thr Thr
        115                 120                 125

Leu Thr Val Ser Ser
    130

<210> SEQ ID NO 77
<211> LENGTH: 133
<212> TYPE: PRT
<213> ORGANISM: Artificial
```

<220> FEATURE:
<223> OTHER INFORMATION: Synthetic

<400> SEQUENCE: 77

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Phe Ala Met His Trp Val Lys Gln Ala Pro Arg Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Gly Thr Ser Ala Ser
                85                  90                  95

Thr Ala Phe Leu Gln Ile Asn Asn Leu Lys Asn Glu Asp Thr Ala Thr
            100                 105                 110

Tyr Phe Cys Ser Ser Asp Pro Leu Asp Tyr Trp Gly Gln Gly Thr Thr
        115                 120                 125

Leu Thr Val Ser Ser
    130

<210> SEQ ID NO 78
<211> LENGTH: 141
<212> TYPE: PRT
<213> ORGANISM: Artificial
<220> FEATURE:
<223> OTHER INFORMATION: Synthetic

<400> SEQUENCE: 78

Met Gly Arg Leu Thr Phe Ser Phe Leu Leu Leu Ile Val Pro Ala Tyr
1               5                   10                  15

Val Leu Cys Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Asn Met Gly Val Val Trp Ile Arg Gln Ser Ser Gly Lys
    50                  55                  60

Gly Leu Glu Trp Leu Leu His Ile Leu Trp Asn Asp Gly Lys Phe Tyr
65                  70                  75                  80

Asn Pro Ala Leu Lys Ser Arg Leu Thr Ile Ser Lys Asp Thr Tyr Asn
                85                  90                  95

Asn Gln Val Phe Leu Lys Ile Ala Asn Val Asp Thr Ala Asp Thr Ala
            100                 105                 110

Thr Tyr Tyr Cys Ala Arg Leu Phe Ser Thr Thr Thr Ser Gly Tyr Phe
        115                 120                 125

Asp Val Trp Gly Ala Gly Thr Thr Val Thr Val Ser Ser
    130                 135                 140

<210> SEQ ID NO 79
<211> LENGTH: 141
<212> TYPE: PRT
<213> ORGANISM: Artificial
<220> FEATURE:
<223> OTHER INFORMATION: Synthetic

<400> SEQUENCE: 79

-continued

```
Met Gly Arg Leu Thr Phe Ser Phe Leu Leu Leu Ile Val Pro Ala Tyr
1               5                   10                  15

Val Leu Cys Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Asn Met Gly Val Val Trp Ile Arg Gln Pro Ser Gly Lys
    50                  55                  60

Gly Leu Glu Trp Leu Leu His Ile Leu Trp Asn Asp Gly Lys Phe Tyr
65                  70                  75                  80

Asn Pro Ala Leu Lys Ser Arg Leu Thr Ile Ser Lys Asp Thr Tyr Asn
            85                  90                  95

Asn Gln Val Phe Leu Lys Ile Ala Asn Val Asp Thr Ala Asp Thr Ala
            100                 105                 110

Thr Tyr Tyr Cys Ala Arg Leu Phe Thr Thr Thr Ser Gly Tyr Phe
        115                 120                 125

Asp Val Trp Gly Ala Gly Thr Thr Val Thr Val Ser Ser
130                 135                 140
```

SPECIFIC BINDING ANTIBODIES OF GLYCOPROTEIN IB ALPHA AS SELECTIVE ECTODOMAIN SHEDDING INHIBITORS

CROSS-REFERENCE TO RELATED APPLICATIONS

This application is the National Stage of International Patent Application No. PCT/US2014/014377 filed Feb. 3, 2014, which claims the benefit of priority to U.S. Provisional Application No. 61/760,249 filed Feb. 4, 2013. The entirety of each of these applications are hereby incorporated by reference for all purposes.

STATEMENT REGARDING FEDERALLY FUNDED RESEARCH

This invention was made with government support under Grants HL082808 and HL097226 awarded by the National Institutes of Health and UL1TR000454 awarded by the National Center for Advancing Translational Sciences. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 13053US_ST25.txt. The text file is 55 KB, was created on Oct. 11, 2017, and is being submitted electronically via EFS-Web.

BACKGROUND

Administration of platelets is a strategy for medical care of patients with thrombocytopenia, e.g., caused by bone marrow dysfunctions or chemotherapy treatments. Platelets are also administered prior to stem cell transplantation. Donated platelets are concentrated and typically stored at 22-24° C. under continuous gentle agitation in bags permeable to oxygen, in order to promote aerobic metabolism instead of glycolysis. However, platelets are not used after the fifth day of storage because of platelet storage lesions and an increased risk of bacterial and viral contamination. Platelets stored at temperatures below 15° C. may slow these undesirable processes; unfortunately, in practice, after administration, they are rapidly cleared from the bloodstream of the recipients. Thus, there is a need to identify improved methods of storing platelets.

Platelet membrane glycoproteins are surface glycoproteins found on platelets (thrombocytes) which play an important role in hemostasis. Glycoprotein Ib-IX-V complex (GPIb-IX-V) contains the subunits: GPIb alpha (GPIbα), GPIb beta (GPIbβ), GPV and GPIX. GPIba subunit bears the binding site for von Willebrand factor (vWF). The binding between GPIba and vWF mediates the capture of platelets to the injured vascular wall. A deficiency in glycoprotein Ib-IX-V complex leads to Bernard-Soulier syndrome, an inherited disease with symptoms of excessive bleeding.

Glycoprotein Ibα (GPIbα) is abundantly expressed on the platelet surface. In addition to its function in mediating ligand-induced platelet activation during primary hemostasis, GPIbα plays a role in thrombosis, thrombocytopenia, inflammation, and other disease states. Nurden et al., Inherited platelet disorders, Haemophilia, 2012, 18(Sup 4): 154-60 and Clemetson & Clemetson, Platelet GPIb complex as a target for anti-thrombotic drug development, Thromb Haemost, 2008, 99: 473-9. GPIbα is continuously proteolyzed in circulating platelets, with its extracellular domain, also known as glycocalicin, released into the plasma. This process is referred to as ectodomain shedding. GPIbα shedding is thought to be an indicator of damaged platelets. GPIbα shedding in platelets can be further stimulated by chemical or physiological agonists, such as Athrombin™, N-(6-aminohexyl)-5-chloro-1-naphthalene sulfonamide (W7, a calmodulin inhibitor that sequesters calmodulin from binding to its ligands), carbonyl cyanide 3-chlorophenylhydrazone (CCCP, a drug that damages the mitochondria and induces apoptosis), and phorbol 12-myristate-13-acetate (PMA).

ADAM17 (A Disintegrin And Metalloprotease 17) is the physiological sheddase for GPIbα. Recombinant ADAM17 cleaves GPIbα based peptides at the Gly464-Val465 peptide bond, suggesting it to be the shedding cleavage site in GPIbα. ADAM17 has broad substrate specificity, and ADAM17 can recognize and cleave a substrate with an extended backbone conformation that is not strictly dependent on any particular side chain. ADAM17 has been shown to cleave physiologically GPIbα, tumor necrosis factor-alpha, and many other substrates with little sequence similarity including Glycoprotein V (GPV).

Broad-spectrum metalloproteinase inhibitors, such as hydroxamic acid-based GM6001 that chelates the zinc ion required for the metalloproteinase activity, strongly inhibit agent induced GPIbα shedding. Gardiner et al. report controlled shedding of platelet glycoprotein (GP)VI and GPIb-IX-V by ADAM family metalloproteinases. J Thromb Haemost, 2007; 5: 1530-7.

Bergmeier et al., report metalloproteinase inhibitors improve the recovery and hemostatic function of in vitro-aged or -injured mouse platelets. Blood, 2003, 102: 4229-35.

Gitz et al. report improved platelet survival after cold storage by prevention of glycoprotein Ibα clustering in lipid rafts. Haematologica, 2012, 97(12): 1873-1881.

Berndt et al. report ristocetin-dependent reconstitution of binding of von Willebrand factor to purified human platelet membrane glycoprotein Ib-IX complex. Biochemistry, 1988, 27: 633-40.

Takayama et al., report anti-platelet membrane glycoprotein VI monoclonal antibodies. See US. Patent Application Number 2011/0217318.

Wagner & Bergmeier report compounds for improving platelet recovery and functions. WO/2004/105837. See also U.S. Pat. No. 8,173,595, WO/2013/096932, WO/2011/162831, and US Patent Application 2013/0216513.

Mo et al. report transmembrane and trans-subunit regulation of ectodomain shedding of platelet glycoprotein Ib alpha. J Biol Chem, 2010, 285(42): 32096-32104.

Liang et al. report specific inhibition of ectodomain shedding of glycoprotein Ibα by targeting its juxtamembrane shedding cleavage site. J Thromb & Haemost, 2013, 11: 2155-2162.

References cited herein are not an admission of prior art.

SUMMARY

This disclosure relates to specific binding agents, such as isolated recombinant monoclonal antibodies, that bind glycoprotein Ib alpha (GPIbα). More specifically, the disclosure relates to methods of preventing platelet ectodomain shedding, preventing platelet clearance and degradation, maintaining and increasing platelet blood serum levels for in vitro or in vivo applications. In some embodiments, the disclosure relates to the production, diagnostic use, and therapeutic use of monoclonal and polyclonal antibodies, and the antigen-binding fragments thereof, which specifically bind GPIbα. Aspects of the disclosure also relate to hybridomas or other cell lines expressing such antibodies for specific binding agent. Compositions and methods for inhibiting protein shedding, platelet clearance, or degradation, or treating diseases associated with GPIbα ectodomain shedding are also described.

In certain embodiments, the disclosure relates to compositions comprising a specific binding agent that inhibits shedding of GPIbα in platelets by binding ADAM17 cleavage site. In certain embodiments, the specific binding agent is an isolated recombinantly produced anti-GPIbα monoclonal antibody (mAb). In certain embodiments, the specific binding agent is a single chain fragment from the antibody of GPIbα, antibody mimetic, GPIbα affibody, or fragment thereof.

The antibody can be a monoclonal antibody, a polyclonal antibody, a recombinant antibody, a humanized antibody, a human antibody, a chimeric antibody, a multi-specific antibody, or an antibody fragment thereof (e.g., a Fab fragment, a Fab' fragment, a F(ab')2 fragment, a Fv fragment, a diabody, or a single chain antibody molecule).

In certain embodiments, the specific binding agent binds the human ADAM17 cleavage site in GPIbα. In certain embodiments, the specific binding agent comprises a polypeptide of SEQ ID NO. 1-16 or variants thereof. In certain embodiments, the polypeptide variants have greater than 50, 60, 70, 80, 85, 90, or 95% sequence identity or similarity to SEQ ID Nos. 1-16. In certain embodiments, variants comprise one, two, three, four, five or six amino acid substitutions. In certain embodiments, the substitutions are not within CDR domains. In certain embodiments, one, two, or three of the substitutions are within CDR domains.

In certain embodiments, the specific binding agent comprises a polypeptide comprising:

a first segment selected from the group, FAFSSYDMS (SEQ ID NO. 18), GYTFTDYAMH (SEQ ID NO. 19), GYTFTDFAMH (SEQ ID NO. 20), and TSNMGVV (SEQ ID NO. 21);

a second segment selected from the group, TISSGGSYT-FYPESVKG (SEQ ID NO. 22), WINTETGEPTYADDFKG (SEQ ID NO. 23), HILWNDGKFYNPALKS (SEQ ID NO. 24); and a third segment selected from the group, LHYNYER-GAVDY (SEQ ID NO. 25), DPLDY (SEQ ID NO. 26), LFSTTTSGYFDV (SEQ ID NO. 27), LFTTTTSGYFDV (SEQ ID NO. 28); or variants thereof.

In certain embodiments, the specific binding agent additional includes or independently comprises a polypeptide comprising, a first segment selected from the group, KASQDINRYLS (SEQ ID NO. 29), KASENVVTYVS (SEQ ID NO. 30), RSSQSLANSYGNTYLS (SEQ ID NO. 31), RSSQSLTNSYGNTYLS (SEQ ID NO. 32), RASGNIHNYLA (SEQ ID NO. 33), RASGNIYNYLA (SEQ ID NO. 34), a second segment selected from the group, RTDRLVE (SEQ ID NO. 35), GASNRYT (SEQ ID NO. 36), EISNRFS (SEQ ID NO. 37), NAETLAD (SEQ ID NO. 38), NAKT-LAD (SEQ ID NO. 39); and a third segment selected from the group, LQYDEFPVT (SEQ ID NO. 40); LQGTHQPWT (SEQ ID NO. 41); QHFWDTPWT (SEQ ID NO. 42); GQGYSYPYT (SEQ ID NO. 43); or variants thereof.

In certain embodiments, the specific binding agent is a humanized monoclonal antibody comprising the CDR regions of 5G6, 15C6, 1H5, 2D2, 2B9, or 3D1.

In certain embodiments, the disclosure relates to isolated recombinant nucleic acid encoding a specific binding agent as disclosed herein. In certain embodiments, the disclosure relates to a vector comprising a recombinant nucleic acid disclosed herein. In certain embodiments, the disclosure relates to expression system comprising the vector of disclosed herein configured to produce a specific binding agent.

In certain embodiments, the disclosure relates to isolated nucleic acid molecules encoding any of the antibodies described herein, vectors having isolated nucleic acid molecules encoding anti-GPIbα antibodies or a host cell transformed with any of such nucleic acid molecules. In addition, one embodiment of the disclosure is a method of producing an anti-GPIbα antibody by culturing host cells under conditions wherein a nucleic acid molecule is expressed to produce the antibody followed by recovering the antibody.

In certain embodiments, the disclosure relates to platelet storage solutions comprising a specific binding agent disclosed herein and a saccharide and a phosphate. In certain embodiments, the saccharide is glucose or citrate. In certain embodiments, the solution has a buffer pH between 5 and 6, 6 and 8, and 8 and 9. In certain embodiments, the storage solution comprises one or more components selected from sodium, potassium, magnesium, citrate, ribose, glucose, maltose, mannitol, phosphate, acetate, gluconate, bovine serum albumin (BSA), tick anticoagulant peptide (TAP), and sterilized water.

In certain embodiments, the disclosure relates to pharmaceutical compositions comprising a specific binding agent disclosed herein. In certain embodiments, disclosure further relates to pharmaceutical compositions comprising the specific binding agent and a pharmaceutically acceptable formulation agent. The pharmaceutical composition may comprise an antibody and a pharmaceutically acceptable formulation agent.

Pharmaceutical compositions of GPIbα specific binding agents or antibodies are within the scope of the present disclosure. In certain embodiments, the disclosure relates to method of preventing platelets from shedding the ectodomain of GPIbα comprising mixing platelets with a specific binding agent disclosed herein under conditions such that the specific binding agent binds the ADAM17 shedding cleavage site or by administering pharmaceutical compositions comprising GPIbα specific binding agents or antibodies that bind to platelets in vivo, e.g., binding to the ADAM17 shedding cleavage site in GPIbα in vivo.

In certain embodiments, the disclosure relates to method of managing a disease or condition associated with GPIbα ectodomain shedding comprising administering an effective amount of a pharmaceutical composition disclosed herein to a subject in need thereof.

In certain embodiments, the subject is at risk of, exhibiting symptoms of, or diagnosed excessive bleeding, with thrombocytopenia, medication-induced thrombocytopenia, heparin-induced thrombocytopenia, Bernard-Soulier syndrome (hemorrhagiparous thrombocytic dystrophy), platelet-type Von Willebrand disease (vWD), Glanzmann's thrombasthenia, or liver failure.

A further embodiment herein includes a method of producing high affinity antibodies to GPIbα by immunizing a mammal with human GPIbα, or a fragment thereof, and one or more orthologous sequences or fragments thereof. In certain embodiments, the method includes a polypeptide of or greater than of 6, 7, 8, 9, 10, 11, 12 amino acids near the ADAM17 cleavage site in GPIbα, typically containing GPIbα Gly464 and Val465 and several surrounding amino acids. In one example, the polypeptide further comprises six or more continuous amino acids in between the human GPIbα sequence Glu455-Phe478 (SEQ ID NO. 52) or GPIbα residues Lys461-Leu470 (SEQ ID NO. 53).

Moreover, in certain embodiments the disclosure relates to a method of detecting the level of GPIbα in a biological sample by (a) contacting a specific binding agent with the sample; and (b) determining the extent of binding of the specific binding agent to the sample.

In certain embodiments, the disclosure contemplates antibodies or a specific binding agent disclosed herein immobilized in a zone, or covalently or non-covalently conjugated to a ligand, biotin, fluorescent dye, fluorescent nanoparticle, or fluorescent protein, or solid surface, e.g., transparent surface, array, hydrogel, polymer, glass, silicon wafer, a magnetic bead. Such surface can be used in methods of purifying platelets.

In certain embodiments, the disclosure contemplates secondary antibodies or secondary binding agents, e.g., an antibody to an anti-GPIbα antibody or a specific binding agent to GPIbα, conjugated to a ligand, biotin, fluorescent dye, fluorescent nanoparticle, or fluorescent protein, or solid surface, e.g., transparent surface, array, hydrogel, polymer, glass, silicon wafer, a magnetic bead. Such surface can be used in methods of purifying platelets having bound antibodies or specific binding agents.

In certain embodiments, the disclosure contemplates epitope polypeptide of antibodies or a specific binding agent binding polypeptide conjugated to a ligand, biotin, fluorescent dye, fluorescent nanoparticle, or fluorescent protein, or solid surface, e.g., transparent surface, array, hydrogel, polymer, glass, silicon wafer, a magnetic bead. Such an epitope polypeptide or binding polypeptide can be used in methods of purifying antibodies and specific binding agents.

Other embodiments of this disclosure will be readily apparent from the disclosure provided herewith.

The shedding-site peptide contains human GPIbα sequence Lys461-Leu470 (SEQ ID NO. 53). (A, C, D) GPIb-IX or the peptide was immobilized in microtiter plates. Purified mAbs, each identified by the clone name and colored as indicated, and negative controls, in the form of mouse IgG or BSA, were added to the coated wells. The bound Ab was detected with biotinylated goat anti-mouse IgG. Data are presented as the mean SD (n=3). (B) Binding plots of various mAbs to washed platelets. Human platelets were incubated with each mAb at indicated concentrations for 20 min and washed once. Binding of mAb was detected by flow cytometry using FITC-conjugated goat anti-mouse IgG and quantitated by mean fluorescence intensity. The plots are representative of three independent experiments.

Figure 1C:
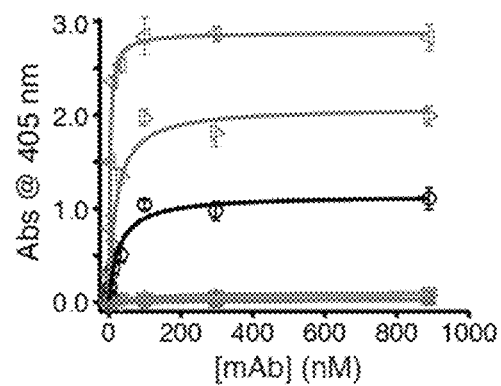
FIG. 1C shows data on the binding of selected monoclonal antibodies (mAbs) to washed human platelet unconjugated.
Figure 1D:
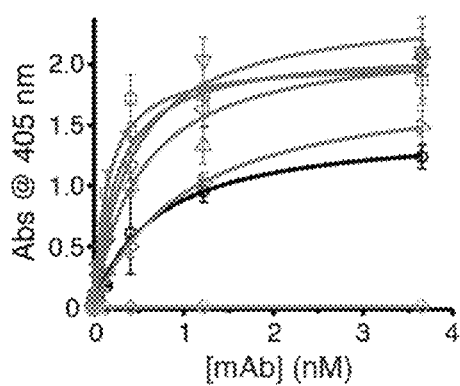
FIG. 1D shows data on the binding of selected monoclonal antibodies (mAbs) to ovalbumin-conjugated shedding-site peptide.
Figure 2A:
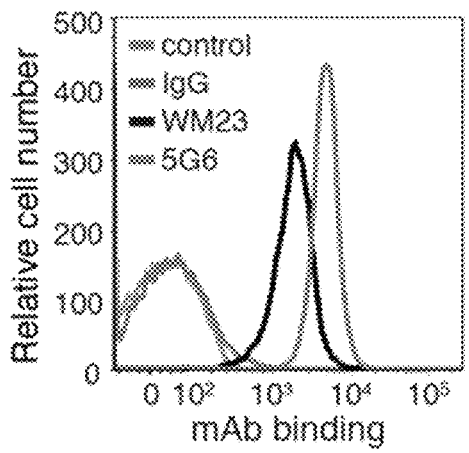

FIG. 2A shows data indicating the clone 5G6 binds specifically to human glycoprotein (GP)Ibα in platelets. Overlaid flow cytometry histograms showing binding of 5G6 to washed human platelets. Human platelets were incubated with 12 nmol $L^{-1}$ of mouse IgG (IgG, green trace), 5G6 (red), or WM23 (black) for 20 min. Binding was detected as described in FIG. 1C. Platelets treated with only FITC-conjugated goat anti-mouse IgG (control, gray) were included as a negative control.

Figure 2B:
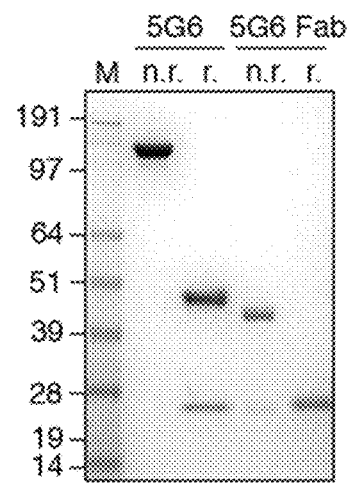

FIG. 2B shows Purity of 5G6 and its Fab fragment shown by 10% Bis-Tris SDS gel electrophoresis under nonreducing (n.r.) and reducing (r.) conditions. Molecular weight markers (M) are shown and labeled in kDa on the left.

Figure 2C:
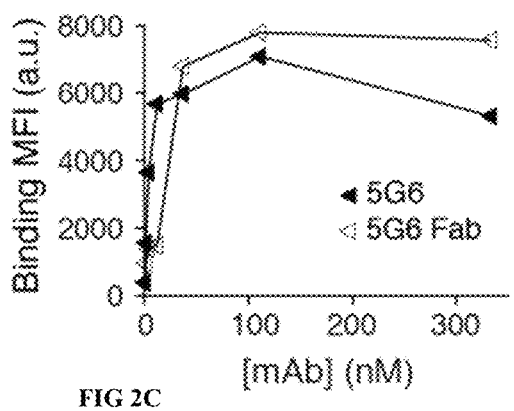

FIG. 2C shows Binding plots of 5G6 and its Fab fragment to washed human platelets. Human platelets were incubated with 5G6 (◄) and biotin-labeled 5G6 Fab (◁) at various concentrations for 20 min. Binding of antibodies was detected by flow cytometry using FITC-conjugated goat anti-mouse IgG (for 5G6) or FITC-conjugated streptavidin (for 5G6 Fab) and quantitated by mean fluorescence intensity (MFI).

Figure 2D:
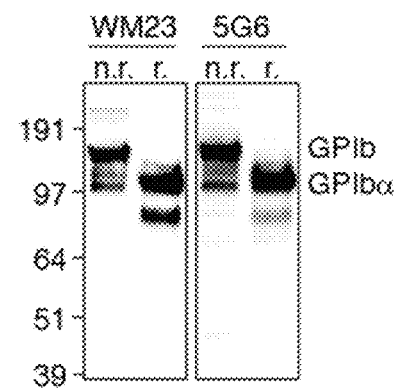

FIG. 2D is Clone 5G6 recognizes specifically GPIbα in Western blot. Total lysates of human platelets were immunoblotted with either WM23 or 5G6. The blots were overexposed to visualize all possible bands blotted by 5G6. Molecular weight markers in kDa are indicated on the left.

Figure 2E:
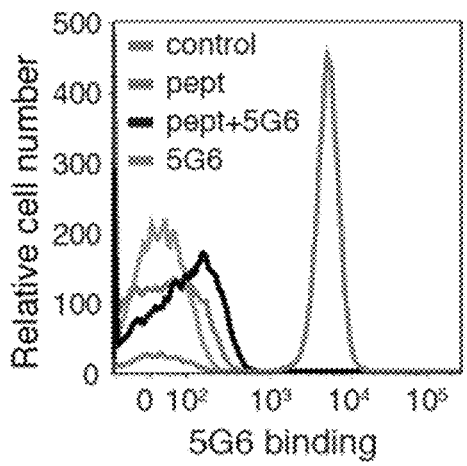

FIG. 2E shows Overlaid flow cytometry histograms showing the competitive inhibition of 5G6 binding to washed human platelets by the shedding-site peptide. Platelets were incubated individually with 7 μmol $L^{-1}$ shedding-site peptide (pept, green trace), 12 nmol $L^{-1}$ 5G6 (red) for 20 min, or 7 μmol $L^{-1}$ shedding site peptide for 20 min followed by 12 nmol $L^{-1}$ 5G6 for another 20 min (pept+5G6, black). Binding was detected as described in FIG. 1C. Negative control was the same as in FIG. 2A.

Figure 2F:
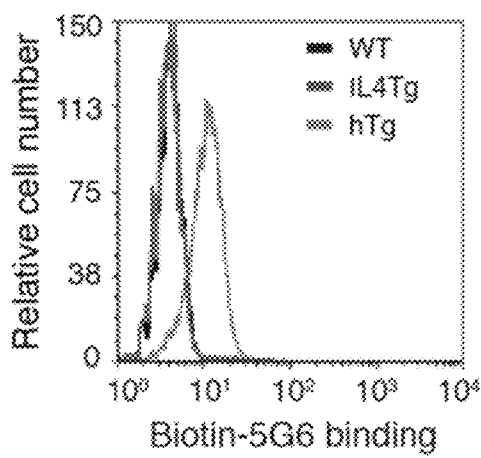

FIG. 2F shows Overlaid flow cytometry histograms showing binding of biotin-labeled 5G6 to transgenic hTg mouse platelets that express only human GPIbα (red trace), but not WT (black) or IL4Tg (blue) mouse platelets that, respectively, express wild-type murine GPIbα and a variant GPIbα where most of the ectodomain of GPIbα was replaced by an isolated domain of the interleukin-4 receptor fused to the transmembrane and cytoplasmic domains of GPIbα. Mouse whole blood was incubated with 4 μg $mL^1$ biotin-labeled 5G6 for 20 min followed by FITC conjugated streptavidin. The binding to platelets was analyzed by flow cytometry with gating specific on platelets. Each figure or histogram is a representative of three independent experiments.

Figure 3A:
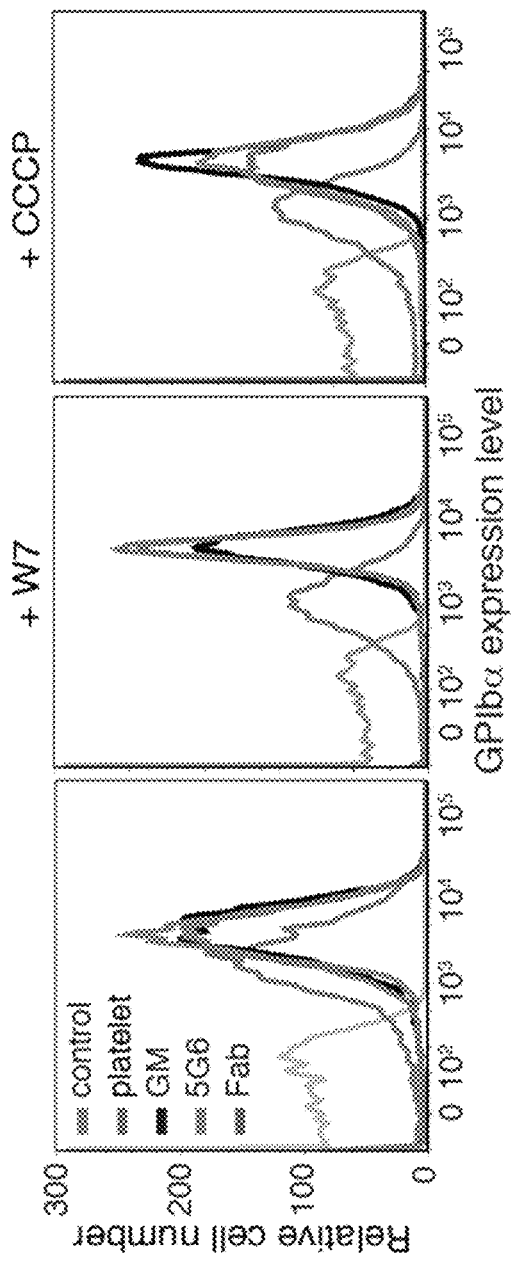

FIG. 3A shows data indicating the clone 5G6 inhibits glycoprotein (GP)Ibα shedding in human platelets. Overlaid flow cytometry histograms showing the inhibition of constitutive and induced shedding of GPIbα by 5G6. Washed human platelets were treated with 5% DMSO (left panel), with 150 μmol $L^{-1}$ W7 (middle) or 100 μmol $L^{-1}$ CCCP dissolved in 5% DMSO (right) in the absence (platelet, green trace) or presence of 12 nmol $L^{-1}$ 5G6 (red), 36 nmol $L^{-1}$ 5G6 Fab fragment (blue), or 100 μmol $L^{-1}$ GM6001 (GM, black) at RT for 2 h. The platelets were then washed and probed for the surface GPIbα expression level using biotin-labeled WM23 and FITC-conjugated streptavidin. Platelets treated only with FITC-conjugated streptavidin (control, gray) as a negative control.

Figure 3B:
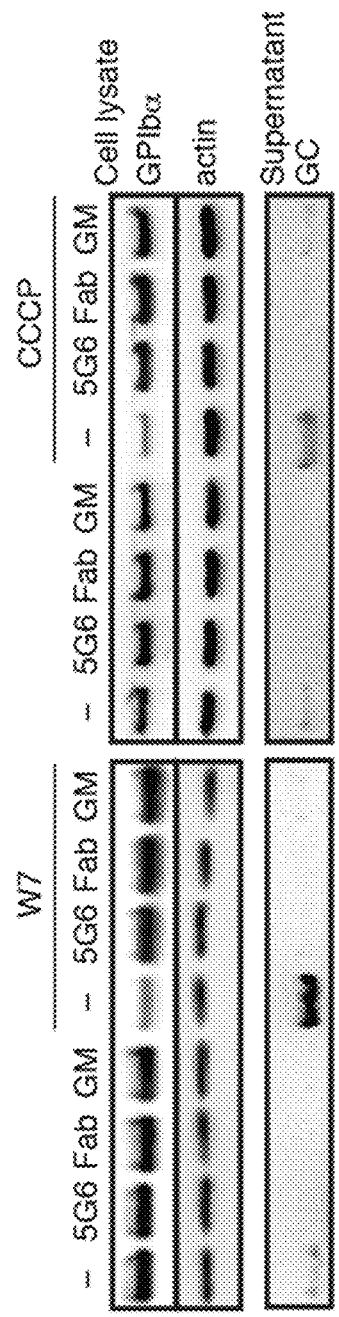

FIG. 3B shows Inhibition of GPIbα shedding by 5G6 assessed by Western blot. Platelets were treated as described in FIG. 3A. Platelet lysate containing full-length GPIbα, and the culture supernatant containing the released glycocalicin (GC), were immunoblotted with WM23. Actin blot of the platelet lysate was included for equal loading control. Each figure or histogram is a representative of three independent experiments.

Figure 4A:
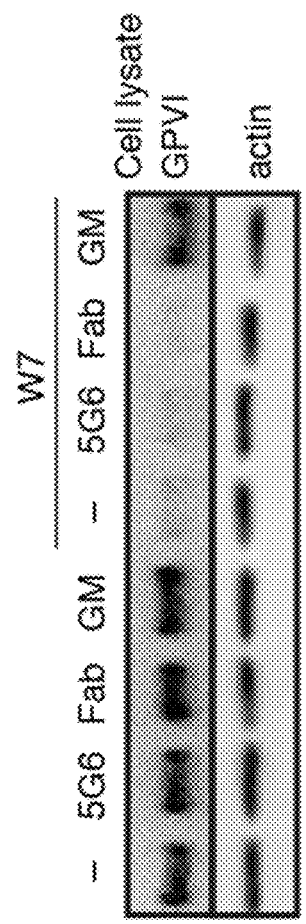

FIG. 4A shows data indicating the clone 5G6 does not inhibit shedding of glycoprotein (GP)V or GPVI in human platelets. 5G6 does not inhibit W7-induced shedding of GPVI. Platelets were treated with W7 as described in FIG. 3A. Platelet lysates were immunoblotted anti-GPVI mAb 6B12. Actin blotting indicates equal sample loading.

Figure 4B:
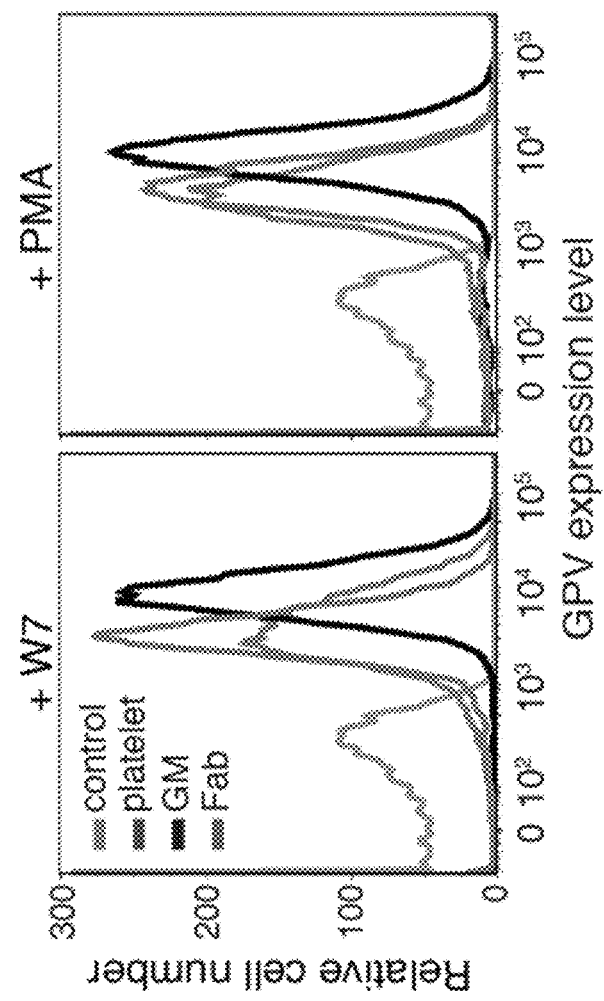

FIG. 4B shows Overlaid flow cytometry histograms showing that 5G6 does not inhibit GPV shedding. Washed platelets were treated with 150 µmol $L^{-1}$ W7 (left panel) or 10 µmol $L^{-1}$ PMA (right) in the absence (platelet, green trace) or presence of 36 nmol $L^{-1}$ 5G6 Fab fragment (Fab, blue) or 100 µmol $L^{-1}$ GM6001 (GM, black) at RT for 2 h. The platelets were then washed and probed for GPV surface expression using anti-GPV mAb SW16 and FITC-conjugated goat anti-mouse IgG. Negative control was same as described in FIG. 2A. Each figure or histogram is a representative of three independent experiments.

FIG. 5A shows data indicating the clone 5G6 exhibits no detectable effect on platelet aggregation and activation. Clone 5G6 does not affect platelet aggregation in platelet-rich plasma (PRP). Left panel, aggregation traces of fresh human PRP after the addition of saline (PRP, blue trace) or 20 nmol $L^{-1}$ 5G6 in saline (PRP+5G6, black). Right, ristocetin-induced aggregation of PRP that had been pretreated with either saline (blue) or 20 nmol $L^{-1}$ 5G6 (black). Ristocetin to a final concentration of 1 mg mL 1 was added at the time point indicated by arrows to induce aggregation.

FIG. 5B shows Overlaid flow cytometry histograms showing that treatment of washed human platelets with 5G6 does not induce platelet activation. Platelet activation is indicated by binding of mAb PAC-1, which is specific for activated integrin aIIbb3 (left panel), increased P-selectin expression on the platelet surface (middle), and binding of GFP-fused C2 domain of lactadherin (GFP-LactC2), which is specific for exposure of phosphoserine lipids (right). Washed platelets were treated with 12 nmol $L^{-1}$ of mouse IgG (control, gray traces) or 5G6 (red) at RT for 10 min and then probed using FITC-conjugated PAC-1, APC conjugated anti-P-selectin Antibody, or GFP-LactC2. Platelets treated with 0.5 U mL$^1$ thrombin or 1 µmol $L^{-1}$ ionomycin were included as positive controls (black traces). The histograms are representative of three independent experiments.

FIG. 6 illustrates certain heavy chain antibody sequence of disclosed antibodies (SEQ ID NO: 74-79). Leader sequence (double underlined)-FR1-CDR1 (underlined)-FR2-CDR2(underlined)-FR3-CDR3(underlined)-FR4 (without leader sequence SEQ ID NO: 1-6 respectively). The double underlined sequences are the leader sequences. They are part of the vector used by the company to clone our variable regions for sequencing.

FIG. 7 illustrates certain light chain antibody sequence of disclosed antibodies (SEQ ID NO: 54-59). Leader sequence (double underlined)-FR1-CDR1 (underlined)-FR2-CDR2 (underlined)-FR3-CDR3(underlined)-FR4 (without leader sequences SEQ ID NO: 7-12 respectively).

FIG. 8 illustrates certain Clone 2B9.B2, IgG2b nucleic acid (SEQ ID NO: 60, 62, and 64, without leader sequences SEQ ID NO: 44, 45, and 46 respectively) and peptide (SEQ ID NO: 61, 63, and 65) sequences of disclosed antibodies. Leader sequence (double underlined)-FR1-CDR1(underlined)-FR2-CDR2(underlined)-FR3-CDR3 (underlined)-FR4 (without leader sequences SEQ ID NO: 2, 8, and 47 respectively).

FIG. 9 illustrates certain Clone 1H5.C3, IgG3 nucleic acid (SEQ ID NO: 66, 68, 70, and 72, without leader sequence 48, 49, 50, and 17 respectively) and peptide (SEQ ID NO: 67, 69, 71, and 73) sequences of disclosed antibodies. Leader sequence (double underlined)-FR1-CDR1(underlined)-FR2-CDR2(underlined)-FR3-CDR3 (underlined)-FR4 (without leader sequences SEQ ID NO: 16, 15, 14, and 13 respectively).

DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

Human GPIbα polypeptide "Glu455-Phe478" refers to ELDQPPKLRGVLQGHLESSRNDPF (SEQ ID NO. 52) and "Lys461-Leu470" refers to KLRGVLQGHL (SEQ ID NO. 53) in SEQ ID NO. 52, and "Gly464-Val465" refers to GV in SEQ ID NO. 52, 53.

As used herein, "subject" refers to any animal, preferably a human patient, livestock, or domestic pet. As used herein, the terms "prevent" and "preventing" include the prevention of the recurrence, spread or onset. It is not intended that the present disclosure be limited to complete prevention. In some embodiments, the onset is delayed, or the severity of the disease is reduced. As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

The terms "polypeptide" and "protein" refer to compounds comprising amino acids joined via peptide bonds and are used interchangeably. Where "amino acid sequence" is recited herein, it to refer to an amino acid sequence of a polypeptide molecule. An "amino acid sequence" can be deduced from the nucleic acid sequence encoding the polypeptide. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycosylations and addition of lipid moieties.

The term "antibody" includes monoclonal antibodies, polyclonal antibodies, recombinant antibodies, humanized antibodies (Jones et al. (1986) Nature 321:522-525; Riechmann et al. (1988) Nature 332:323-329; and Presta (1992) Curr. Op. Struct. Biol. 2:593-596), chimeric antibodies (Morrison et al. (1984) Proc. Natl. Acad. Sci. US 81:6851-6855), multispecific antibodies (e.g., bispecific antibodies) formed from at least two antibodies, or antibody fragments thereof. The term "antibody fragment" comprises any portion of the afore-mentioned antibodies, such as their antigen binding or variable regions. Examples of antibody fragments include Fab fragments, Fab' fragments, F(ab')2 fragments, Fv fragments, diabodies (Hollinger et al. (1993) Proc. Natl. Acad. Sci. US 90:6444-6448), single chain antibody molecules (Pluckthun in: The Pharmacology of Monoclonal Antibodies 113, Rosenburg and Moore, eds., Springer Verlag, NY (1994), 269-315) and other fragments as long as they exhibit the desired capability of binding to GPIbα.

An "Fv fragment" is the minimum antibody fragment that contains a complete antigen-recognition and -binding site. This region consists of a dimer of one heavy chain variable domain and one light chain variable domain in tight, non-covalent association. It is in this configuration that the three CDR's of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain (CH1) of the heavy chain. The "Fab fragment" differs from the "Fab' fragment" by the addition of a few residues at the carboxy terminus of the heavy chain CH1 domain, including one or more cysteines from the antibody hinge region. The "F(ab')2 fragment" originally is produced as a pair of "Fab' fragments" which have hinge cysteines between them. Methods of preparing such antibody fragments, such as papain or pepsin digestion, are known to those skilled in the art.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, small regulatory RNAs, operon sequences and smaller engineered nucleotide sequences that express or may be adapted to express, proteins, polypeptides or peptides.

The term "a nucleic acid sequence encoding" a specified polypeptide refers to a nucleic acid sequence comprising the coding region of a polypeptide or in other words the nucleic acid sequence which encodes a polypeptide product. The coding region may be present in either cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements. The term "cDNA" refers to complementary DNA (cDNA), i.e., DNA synthesized from a RNA (e.g. mRNA) template typically catalyzed by the enzymes reverse transcriptase and DNA polymerase.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

A "cloning vector" refers to a nucleic acid molecule used as a vehicle to carry foreign genetic material into another cell, where it can be replicated and/or expressed. Examples of vectors are plasmids, viral vectors, cosmids, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs) are for the expression of the transgene in the target cell, and generally have a promoter sequence that drives expression of the transgene. Insertion of a vector into the target cell is referred to transformation or transfection for bacterial and eukaryotic cells, although insertion of a viral vector is often called transduction.

Polypeptide "expression systems" refer to in vivo and in vitro (cell free) systems. Systems for recombinant polypeptide expression typically utilize cells transfecting with a DNA expression vector that contains the template. The cells are cultured under conditions such that they translate the desired polypeptide. Expressed polypeptides are extracted for subsequent purification. In vivo polypeptide expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize polypeptides of interest. Cell-free systems typically do not contain proteases and enable labeling of the polypeptide with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

Specific Inhibition of Ectodomain Shedding of Glycoprotein Ibα by Targeting its Juxtamembrane Shedding Cleavage Site Disclosed herein are anti-GPIbα monoclonal antibodies (mAbs) that specifically inhibit shedding of human GPIbα in platelets. GPIbα is continuously shed from the platelet surface. The biological significance of GPIbα shedding remains to be defined, although it has been linked to platelet clearance. Reagents that specifically inhibits shedding of GPIbα has been developed. The monoclonal antibody 5G6 targets the shedding cleavage site in human GPIbα and is able to block shedding of human GPIbα in platelets (FIGS. 2 and 3). The antigen specificity of the monoclonal antibody limits the inhibitory effect of 5G6 on only GPIbα shedding (FIG. 4). Moreover, 5G6 binding neither activates platelets nor affect platelet activation induced by ristocetin (FIG. 5) and other agonists.

Ectodomain shedding affects a diverse array of transmembrane proteins. With the well-documented broad substrate specificity of ADAM sheddases, it is not surprising that modulating the activity of ADAM sheddase with inhibitors, even specifically that of ADAM17, often results in systemic changes or unwanted toxicity. Modulating the ADAM activity also does not provide the definitive answer about the significance of shedding of individual receptors. Targeting directly the shedding cleavage site of a shedding substrate can achieve substrate-specific inhibition of ectodomain shedding.

The shedding cleavage site in GPIbα is located in a juxtamembrane stalk region that is thought to be structurally flexible. In the platelet, GPIbα associates closely with GPIbβ, GPIX, and GPV, mostly through their transmembrane domains, to form the GPIb-IX-V complex. While the detailed structural information is lacking, the GPIbα stalk region is may locate next to, and interact with, GPIbβ and GPIX extracellular domains that are tightly integrated with one another. Nonetheless, 5G6 and other selected mAbs are able to bind the shedding cleavage site in the full-length functional complex, indicating that the cleavage site in GPIbα is accessible to antibody binding.

Methods of Use

In certain embodiments, the disclosure relates to method of preventing platelets from shedding the ectodomain of GPIbα comprising mixing platelets with a specific binding agent disclosed herein under conditions such that the specific binding agent binds the ADAM17 shedding cleavage site. In certain embodiments, within any of the uses and methods disclosed herein the specific binding agent that inhibits shedding of GPIbα in platelets by binding ADAM17 shedding cleavage site is an antibody, single chain binding fragment, or antibody mimetic that binds human GPIbα polypeptide Glu455-Phe478 (SEQ ID NO. 52) or GPIbα residues Lys461-Leu470 (SEQ ID NO. 53) or a fragment thereof.

Platelets are typically stored under continuous gentle agitation in plasticized polyvinylchloride bags with di-(2-ethylhexyl) phthalate (DEHP), which are permeable to oxygen, in order to promote aerobic metabolism instead of glycolysis. Platelets stored at temperatures below 15° C. perform very poorly, mainly due to an elevated percentage of cold stored platelet being rapidly cleared from the bloodstream of the recipients. In certain embodiments, the disclosure relates to polymeric container permeable to oxygen comprising specific binding agents disclosed herein, e.g., a polyvinylchloride container with di-(2-ethylhexyl) phthalate (DEHP), which are permeable to oxygen, in order to promote aerobic metabolism instead of glycolysis comprising specific binding agents disclosed herein.

In one aspect of this embodiment, an improved blood product is prepared by incorporating a specific binding agent or antibody disclosed herein in a platelet preparation, and preferably a platelet storage container for the blood product, in an amount effective to prevent the cleavage of platelet GPIbα from the platelets. In another aspect of this embodiment, the improved blood product is prepared by incorporating a specific binding agent or antibody disclosed herein in a platelet preparation in order to prevent cleavage or shedding of platelet glycoprotein GPIbα from the platelets while maintained in a suitable storage container.

The improvements resulting from this embodiment of the disclosure include enhanced platelet recovery, and the preservation of platelet hemostatic function of the stored platelets. In certain embodiments, the disclosure relates to an improved blood product for use in transfusions in circumstances where blood is needed as a part of the medical treatment of a subject.

In another embodiment, the present disclosure relates to a process for storing a blood product containing platelets. In one aspect, the stored blood product can contain a specific binding agent or antibody disclosed herein. The treated platelets are stored in a suitable storage container for a time period of from about 3 or 5 days to about 10 days, and preferably for about 5 days, prior to use in a transfusion. The recovery of platelets is improved following storage, and the hemostatic function of the platelets is preserved, as compared to untreated platelets.

In certain embodiments, the platelets are stored at temperatures significantly reduced ("chilled") from standard platelet storage temperatures, e.g., less than about 22° C., and preferably from about 15° C. to 0° C. to about 4° C., to reduce the metabolic activity of the platelets. In certain embodiments, the platelet are frozen, e.g., dimethyl sulfoxide (DMSO), and stored for extended periods at less than 0° C. to about negative 80° C.

In a further embodiment, the present disclosure relates to a method for treating a patient by administering to the patient the improved blood product disclosed herein. In certain embodiments, the present disclosure relates to a method for treating a patient by administering to the patient the specific binding agent disclosed herein for a therapeutically effective in vivo response.

In a yet further embodiment, the disclosure relates to a method for testing the quality of stored platelets by determining the level of expression of GPIbα on the platelet surface, with a low level of GPIbα indicating inferior quality and inferior biological competence of the stored platelets. Preferably, this is accomplished in the blood bank prior to the infusion of the platelet concentrate in the patient.

In certain embodiments, the disclosure relates to method of managing a disease or condition associated with GPIbα ectodomain shedding comprising administering an effective amount of either specific binding agents and antibodies disclosed herein or the product of platelets mixed with specific binding agents and antibodies disclosed herein to provide specific binding agent bound platelets or antibody bound platelets to a subject in need thereof.

In certain embodiments, the subject is at risk of, exhibiting symptoms of, or diagnosed with thrombocytopenia, medication-induced thrombocytopenia, heparin-induced thrombocytopenia, hemorrhagiparous thrombocytic dystrophy, Platelet-type Von Willebrand disease (vWD), Glanzmann's thrombasthenia, or liver failure. In certain embodiments, the subject is at risk of, exhibiting symptoms of, or diagnosed with thrombocytopenia caused by bone marrow dysfunctions or chemotherapy treatments. In certain embodiments, the specific binding agent bound platelets or antibody bound platelets are administered prior to, after, or during a surgical procedure, e.g., organ, tissue or cell transplantation, stem cell transplantation, extracorporeal circulation during transplant surgery, abdominal surgery, vascular surgery, or cardiopulmonary bypass surgery.

In certain embodiments, the disclosure relates to method of treating or preventing inflammation, sepsis, or endotoxemia comprising administering an effective amount of a specific binding agent disclosed herein to a subject in need thereof.

In certain embodiments, the disclosure relates to methods of treating cancer comprising administering a pharmaceutical composition comprising a specific binding agent disclosed herein to a subject in need thereof. In certain embodiments, the cancer is leukemia, lymphoma, and myeloma.

In certain embodiments, undesirable ectodomain shedding may result in abnormally low platelet counts, e.g., a subject with lower than 150,000 counts per μL (microliter) of blood. Abnormally low platelet counts may affect blood clotting and wound repair. Thus, in certain embodiments, the disclosure contemplates managing, treating or preventing platelet, coagulation, or wound repair diseases, conditions, abnormalities, whether genetic or acquired. Contemplated diseases or conditions include, for example, thrombocytopenia, medication-induced thrombocytopenia, heparin-induced thrombocytopenia, HIV-associated thrombocytopenia, hemorrhagiparous thrombocytic dystrophy, Platelet-type Von Willebrand disease (vWD), Glanzmann's thrombasthenia, liver failure, dengue fever, immune thrombocytopenic purpura, gestational thrombocytopenia, preeclampsia/eclampsia syndrome, posttransfusion purpura, neonatal alloimmune thrombocytopenia, systemic lupus erythematosus, antiphospholipid syndrome, disseminated intravascular coagulopathy, and hemolytic-uremic syndrome.

Also contemplated is a combination therapy as a method of treating conditions or diseases disclosed herein in a mammal comprising administering a therapeutically effective amount of a specific binding agent or antibody described herein in combination with a second therapeutic agent, e.g., anti-thrombotic, aspirin, heparin, heparin sulfate, enoxaparin, dalteparin, tinzaparin, ticlopidine, clopidogrel, tirofiban, dipyridamole, anagrelide, epoprostenol, eptifibatide, cilostazol, abciximab, platelet activating agent, thromboxane, epinephrine, a chemotherapy agent or medications that induce thrombocytopenia, e.g., quinidine, amiodarone, gold, captopril, sulfonamides, glyburide (glibenclamide), carbamazepine, ibuprofen, cimetidine, tamoxifen, ranitidine, phenytoin, vancomycin, or piperacillin. In certain embodiments, a specific binding agent is administered during or after the administration of an anti-thrombotic or medications that induce thrombocytopenia to counteract or minimize effects.

Contemplated chemotherapy agents include temozolamide, gefitinib, erlotinib, docetaxel, cisplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, lenalidomide, or combinations thereof.

Specific Binding Agents

In certain embodiments, the disclosure relates to compositions comprising a specific binding agent that inhibits shedding of GPIbα in platelets by binding ADAM17 shedding cleavage site.

In certain embodiments, the specific binding agent is an isolated recombinantly produced anti-GPIbα monoclonal antibody (mAb). In certain embodiments, the specific binding agent binds the human ADAM17 shedding cleavage site. In certain embodiments, the specific binding agent comprises a polypeptide of SEQ ID NO. 1-16 or variants thereof. In certain embodiments, variants comprises one, two, three, four, five or six amino acid substitutions. In certain embodiments, the substitutions are not within CDR domains. In certain embodiments, one, two, or three of the substitutions are within CDR domains.

In certain embodiments, the specific binding agent comprises a polypeptide comprising:

a first segment selected from the group, FAFSSYDMS (SEQ ID NO. 18), GYTFTDYAMH (SEQ ID NO. 19), GYTFTDFAMH (SEQ ID NO. 20), and TSNMGVV (SEQ ID NO. 21);

a second segment selected from the group, TISSGGSYTFYPESVKG (SEQ ID NO. 22), WINTETGEPTYADDFKG (SEQ ID NO. 23), HILWNDGKFYNPALKS (SEQ ID NO. 24); and a third segment selected from the group, LHYNYERGAVDY (SEQ ID NO. 25), DPLDY (SEQ ID NO. 26), LFSTTTSGYFDV (SEQ ID NO. 27), LFTTTTSGYFDV (SEQ ID NO. 28); or variants thereof.

In certain embodiments, the specific binding agent additional includes or independently comprises a polypeptide comprising, a first segment selected from the group, KASQDINRYLS (SEQ ID NO. 29), KASENVVTYVS (SEQ ID NO. 30), RSSQSLANSYGNTYLS (SEQ ID NO. 31), RSSQS- LTNSYGNTYLS (SEQ ID NO. 32), RASGNIHNYLA (SEQ ID NO. 33), RASGNIYNYLA (SEQ ID NO. 34), a second segment selected from the group, RTDRLVE (SEQ ID NO. 35), GASNRYT (SEQ ID NO. 36), EISNRFS (SEQ ID NO. 37), NAETLAD (SEQ ID NO. 38), NAKTLAD (SEQ ID NO. 39); and a third segment selected from the group, LQYDEFPVT (SEQ ID NO. 40); LQGTHQPWT (SEQ ID NO. 41); QHFWDTPWT (SEQ ID NO. 42); GQGYSYPYT (SEQ ID NO. 43); or variants thereof.

In certain embodiments, the specific binding agent is a humanized monoclonal antibody comprising the CDR regions of 5G6, 15C6, 1H5, 2D2, 2B9, or 3D1.

In certain embodiments, the disclosure contemplates specific binding agents containing the aforementioned polypeptide sequences. A specific binding agent can be a scaffold protein having an antibody-like binding activity (e.g., having activity similar to an anti-GPIbα antibody) or an antibody, i.e., an anti-GPIbα antibody.

As used herein, the term "scaffold protein" means a polypeptide or protein with exposed surface areas in which amino acid insertions, substitutions or deletions are highly tolerable. Examples of scaffold proteins that can be used in accordance with the present methods include protein A from *Staphylococcus aureus*, the bilin binding protein from *Pieris brassicae* or other lipocalins, ankyrin repeat proteins, and human fibronectin. Engineering of a scaffold protein can be regarded as grafting or integrating an affinity function onto or into the structural framework of a stably folded protein. Affinity function means a protein binding affinity according to the present document. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against GPIbα, either purified protein or protein displayed on the cell surface, for binding agents in an artificial scaffold library displayed in vitro, skills which are known in the art. In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. The inserted binding domains may be, for example, the complementarity determining region (CDR) of an antibody, in particular an anti-GPIbα antibody. Insertion can be accomplished by various methods known to those skilled in the art including, for example, polypeptide synthesis, nucleic acid synthesis of an encoding amino acid as well by various forms of recombinant methods well known to those skilled in the art.

In certain embodiments, the disclosure contemplates antibodies that are polyclonal, monoclonal, chimeric, humanized, or fully human antibodies. They are single chain antibody as well as multi-chain antibodies. Hybridomas that produce the monoclonal antibodies are also contemplated, as well as, nucleic acid molecules encoding the polypeptides and the antibodies, the vectors containing these nucleic acid molecules, and the host cells, such as CHO cells, that contain and express them. A method of making a binding agent or an antibody of the present disclosure comprises transforming a host cell with at least one nucleic acid molecule encoding the binding agent or antibody; expressing the nucleic acid molecule in said host cell; and isolating said specific binding agent or antibody.

In a further embodiment, the disclosure is an isolated antibody which comprises a heavy chain and a light chain, wherein the heavy chain comprises a heavy chain variable domain and the light chain comprises a light chain variable domain, wherein the heavy chain comprises 3 heavy chain (HC) CDRs and said light chain variable domain comprises 3 light chain (LC) CDRs, wherein the sequences of said HC and LC CDRs of the antibody are selected from the group consisting of:

(a) 1H5.C3—SEQ ID NOs: 18, 22, 25 of the HC plus SEQ ID NOs: 29, 35, 40 of the LC, (b) 2B9.B2, 2D2.E3—SEQ ID NOs: 19, 23, 26 of the HC plus SEQ ID NOs: 31, 37, 41 of the LC, (c) 2B9.B2—SEQ ID NOs: 19, 23, 26 of the HC plus SEQ ID NOs: 30, 36, 43 of the LC, (d) 3D1.E3—SEQ ID NOs: 20, 23, 27 of the HC plus SEQ ID NOs: 32, 37, 41 of the LC, (e) 15C6.D3—SEQ ID NOs: 21, 24, 27 of the HC plus SEQ ID NOs: 33, 38, 42 of the LC, (f) 5G6.B4—SEQ ID NOs: 21, 24, 28 of the HC plus SEQ ID NOs: 34, 39, 42 of the LC;

wherein the antibody specifically binds to GPIbα.

The present disclosure also is directed to an antibody having a heavy chain and light chain, where the light chain has a light chain variable domain having three LC CDRs of any one of (a) through (f), supra, wherein the antibody specifically binds to GPIbα.

Additionally, the present disclosure also is directed to an antibody having a heavy chain and light chain, where the heavy chain has a heavy chain variable domain having three HC CDRs of any one of (a) through (f), supra, wherein the antibody specifically binds to GPIbα.

The present disclosure also is directed to a specific binding agent, single chain antibody, or other antibody having three HC CDRs of any one of (a) through (f), supra, wherein the binding agent binds specifically to GPIbα. In certain embodiments, the antibody is a single chain antibody fusion antibody conjugated to an IgG.

Additionally, the present disclosure also is directed to a specific binding agent, single chain antibody, or other antibody having three LC CDRs of any one of (a) through (f), supra, wherein the binding agent binds specifically to GPIbα. In certain embodiments, the antibody is a single chain antibody fusion antibody conjugated to an IgG.

One embodiment of the disclosure, the specific binding agent is a fully human antibody that specifically binds to GPIbα and prevents ADAM17 binding to GPIbα. Yet another embodiment of the disclosure is a fully human monoclonal antibody that binds to GPIbα and also inhibits ectodomain shedding. The antibody may bind GPIbα with a Kd of less than about 100 nM, 100 pM, 30 pM, 20 pM, 10 pM, 5 pM or 1 pM. Certain embodiments of the disclosure are antibodies of the IgA-, IgD-, IgE, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type.

It is to be understood that the amino acid sequence of the specific binding agents provided herein is not limited to the twenty conventional amino acids. For example, the amino acids may include stereoisomers (e.g., D-amino acids) of the twenty conventional amino acids, unnatural amino acids such as alpha-,alpha-disubstituted amino acids, N-alkyl amino acids, lactic acid, and other unconventional amino acids. Examples of unconventional amino acids, which may also be suitable components for the binding proteins provided herein, include: 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, sigma-N-methylarginine, and other similar amino acids and imino acids, e.g., 4-hydroxyproline.

Another embodiment of the disclosure provides a binding agent such as an antibody comprising a heavy chain and a light chain, wherein said heavy chain comprises a heavy chain variable region selected from the group consisting of H1 (1H5.C3, SEQ ID NO. 1); H2 (2B9.B2, SEQ ID NO. 2); H3 (2D2.E3, SEQ ID NO. 3); H4 (3D1.C1, SEQ ID NO. 4); H5 (15C6.D3, SEQ ID NO. 5); H6 (5G6.B4, SEQ ID NO. 6); and antigen binding fragments thereof; and said light chain comprises a light chain variable region selected from the group consisting of: L1 (1H5.C3, SEQ ID NO. 7); L2 (2B9.B2, SEQ ID NO. 8); L3 (2D2.E3, SEQ ID NO. 9); L4 (3D1.C1, SEQ ID NO. 10); L5 (15C6.D3, SEQ ID NO. 11); L6 (5G6.B4, SEQ ID NO. 12) and antigen binding fragments thereof. In certain embodiments, any of the sequences, SEQ ID NO. 1-16, may have one, two, three, four, five, or six amino acid substitutions. In certain embodiments, the substitutions are not within the CDR 1, 2, or 3. In certain embodiments, the one or two substitutions are within the CDR 1. In certain embodiments, the one or two substitutions are within the CDR 2. In certain embodiments, the one or two substitutions are within the CDR 3. In certain embodiments, the substitutions are conservative substitutions.

The disclosure also provides a specific binding agent comprising at least one peptide selected from the group consisting of: H1 (SEQ ID NO. 1); H2 (SEQ ID NO. 2); H3 (SEQ ID NO. 3); H4 (SEQ ID NO. 4); H5 (SEQ ID NO. 5); H6 (SEQ ID NO. 6); L1 (SEQ ID NO. 7); L2 (SEQ ID NO. 8); L3 (SEQ ID NO. 9); L4 (SEQ ID NO. 10); L5 (SEQ ID NO. 11); L6 (SEQ ID NO. 12); and antigen binding fragments thereof. In certain embodiments, any of the sequences, SEQ ID NO. 1-16, may have one, two, three, four, five, or six amino acid substitutions. In certain embodiments, the substitutions are not within the CDR 1, 2, or 3. In certain embodiments, the one or two substitutions are within the CDR 1. In certain embodiments, the one or two substitutions are within the CDR 2. In certain embodiments, the one or two substitutions are within the CDR 3. In certain embodiments, the substitutions are conservative substitutions.

It will be appreciated that the specific binding agent can be, for example, an antibody, such as a polyclonal, monoclonal, chimeric, humanized, or a fully human antibody. The antibody may also be a single chain antibody. Other examples of specific binding agents include peptibodies, avimers, other forms of peptide molecules, such as Fc-fusion molecules and Ab-fusion molecules that contain peptide sequences which recognize and bind to a protein target (in this context, GPIbα), etc.

A specific embodiment of the disclosure relates to peptibodies that bind GPIbα. Other embodiments of the disclosure include GPIbα-binding peptides that can be made by addition, deletion, and/or insertion of amino acids to peptide sequences disclosed herein. Further alterations to the sequences are taught in, for example, WO00/24782 and WO03/057134 which are incorporated herein by reference to the sections which describe and teach making binding agents that contain a randomly generated peptide which binds a desired target.

In certain embodiments, disclosure further relates to a specific binding agent comprising heavy chain complementarity determining region 1 (CDR 1) of any of: FAFSSYDMS (SEQ ID NO. 18); GYTFTDYAMH (SEQ ID NO. 19); GYTFTDFAMH (SEQ ID NO. 20); and TSNMGVV (SEQ ID NO. 21). In certain embodiments, one or two of the amino acids of are substituted. In certain embodiments, the substitutions are conservative substitutions.

In certain embodiments, disclosure further relates to a specific binding agent comprising heavy chain complementarity determining region 2 (CDR 2) of any of: TISSGGSYTFYPESVKG (SEQ ID NO. 22); WINTETGEPTYADDFKG (SEQ ID NO. 23); HILWNDGKFYNPALKS (SEQ ID NO. 24). In certain embodiments, one or two of the amino acids of are substituted. In certain embodiments, the substitutions are conservative substitutions.

In certain embodiments, disclosure further relates to a specific binding agent comprising heavy chain complementarity determining region 3 (CDR 3) of any of: LHYNYERGAVDY (SEQ ID NO. 25); DPLDY (SEQ ID NO. 26); LFSTTTSGYFDV (SEQ ID NO. 27); LFTTTTSGYFDV (SEQ ID NO. 28). In certain embodiments, one or two of the amino acids of are substituted. In certain embodiments, the substitutions are conservative substitutions.

In certain embodiments, disclosure further relates to a specific binding agent comprising light chain complementarity determining region 1 (CDR 1) of any of: KASQDINRYLS (SEQ ID NO. 29); KASENVVTYVS (SEQ ID NO. 30); RSSQSLANSYGNTYLS (SEQ ID NO. 31); RSSQSLTNSYGNTYLS (SEQ ID NO. 32); RASGNIHNYLA (SEQ ID NO. 33); RASGNIYNYLA (SEQ ID NO. 34). In certain embodiments, one or two of the amino acids of are substituted. In certain embodiments, the substitutions are conservative substitutions.

In certain embodiments, disclosure further relates to a specific binding agent comprising light chain complementarity determining region 2 (CDR 2) of any of: RTDRLVE (SEQ ID NO. 35); GASNRYT (SEQ ID NO. 36); EISNRFS (SEQ ID NO. 37); NAETLAD (SEQ ID NO. 38); NAKTLAD (SEQ ID NO. 39). In certain embodiments, one or two of the amino acids of are substituted. In certain embodiments, the substitutions are conservative substitutions.

In certain embodiments, disclosure further relates to a specific binding agent comprising light chain complementarity determining region 3 (CDR 3) of any of: LQYDEFPVT (SEQ ID NO. 40); LQGTHQPWT (SEQ ID NO. 41); QHFWDTPWT (SEQ ID NO. 42); GQGYSYPYT (SEQ ID NO. 43). In certain embodiments, one or two of the amino acids of are substituted. In certain embodiments, the substitutions are conservative substitutions.

In certain embodiments, the disclosure further relates to a hybridoma that produces a monoclonal antibody according to the disclosure, as well as a cell lines confining (through any means such as by transfection, transformation, electroporation) with the nucleic acid sequences necessary to express the present specific binding agents such as the antibodies described herein.

In some embodiments, a specific binding protein can be prepared recombinantly by optimizing and/or amplifying expression of the binding protein in host cells, and isolating the binding protein from the host cells. To this end, host cells can be transformed or transfected with DNA (e.g., a vector) encoding a specific binding protein, and cultured under conditions appropriate to produce the binding protein. Useful host cells include, for example, CHO cells, human embryonic kidney 293 cells, *E. coli* cells, and *Saccharomyces cerevisiae* cells.

Specific binding proteins that are antibodies can be prepared from animals genetically engineered to make fully human antibodies, or from an antibody display library made in bacteriophage, yeast, ribosome or E. coli.

In some embodiments, antibodies as provided herein can be fully human or humanized antibodies. Human antibodies avoid certain problems associated with xenogeneic antibodies, such as antibodies that possess murine or rat variable and/or constant regions. The presence of xenogeneic-derived proteins can lead to an immune response against the antibody by a patient, subsequently leading to the rapid clearance of the antibody, loss of therapeutic utility through neutralization of the antibody, and/or severe, even life-threatening, allergic reactions. To avoid the using murine or rat-derived antibodies, fully human antibodies can be generated through the introduction of functional human antibody loci into a rodent or another mammal or animal so that the rodent, other mammal or animal produces fully human antibodies.

One method for generating fully human antibodies is to utilize XENOMOUSE™ strains of mice that have been engineered to contain 245 kb and 190 kb-sized germline configuration fragments of the human heavy chain locus and kappa light chain locus. Other XENOMOUSE™ strains of mice contain 980 kb and 800 kb-sized germline configuration fragments of the human heavy chain locus and kappa light chain locus. Still other XENOMOUSE™ strains of mice contain 980 kb and 800 kb-sized germline configuration fragments of the human heavy chain locus and kappa light chain locus plus a 740 kb-sized germline configured complete human lambda light chain locus. See US Patent Publication 2003/0217373 and U.S. Pat. Nos. 5,939,598, 6,075,181, 6,114,598, 6,150,584, 6,162,963, 6,673,986, 6,833,268, and 7,435,871.

Alternatively, a "minilocus" approach can be used. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (e.g., a gamma constant region) are formed into a construct for insertion into an animal. This approach is described in U.S. Pat. Nos. 5,545,806, 5,545,807, 5,569,825, 5,591,669, 5,612,205, 5,625,126, 5,625,825, 5,633,425, 5,643,763, 5,661,016, 5,721,367, 5,770,429, 5,789,215, 5,789,650, 5,814,318, 5,874,299, 5,877,397, 5,981,175, 6,023,010, 6,255,458.

Human antibodies also can be derived by in vitro methods. Suitable examples include, but are not limited to, phage display (as commercialized by Cambridge Antibody Technology™, Morphosys™, Dyax™, Biosite/Medarex™, Xoma™, Symphogen™, Alexion™ (formerly Proliferon), and Affimed™), ribosome display (as commercialized by Cambridge Antibody Technology™), yeast display, and the like.

Using technology as described herein, fully human monoclonal antibodies to a variety of antigens can be produced. For example, XENOMOUSE™ lines of mice can be immunized with a GPIbα antigen of interest (e.g., human GPIbα Glu455-Phe478 (SEQ ID NO. 52) or GPIbα residues Lys461-Leu470 (SEQ ID NO. 53) or a fragment thereof), lymphatic cells (such as B-cells) can be recovered from mice that express antibodies, and the recovered cell lines can be fused with a myeloid-type cell line to prepare immortal hybridoma cell lines. These hybridoma cell lines can be screened and selected to identify hybridoma cell lines that produce antibodies specific to the antigen of interest. Provided herein are methods for the production of multiple hybridoma cell lines that produce antibodies specific to Glu455-Phe478 (SEQ ID NO. 52) or GPIbα residues Lys461-Leu470 (SEQ ID NO. 53). Further provided herein are methods for characterizing antibodies produced by such cell lines, including nucleotide and amino acid sequence analyses of the heavy and light chains of such antibodies.

It will also be appreciated that the disclosure relates to conjugates as described herein. The conjugate can be, for example, a specific binding agent (such as an antibody) of the disclosure conjugated to other proteinaceous, carbohydrate, lipid, or mixed moiety molecule(s).

The disclosure further relates to nucleic acid molecules encoding the specific binding agents (such as an antibody), as well as a vector comprising such nucleic acid molecule, as well as a host cell containing the vector.

Additionally, the disclosure provides a method of making a specific binding agent comprising, (a) transforming a host cell with at least one nucleic acid molecule encoding the specific binding agent; (b) expressing the nucleic acid molecule in said host cell; and (c) isolating said specific binding agent. In certain embodiments, the disclosure further provides a method of making an antibody comprising: (a) transforming a host cell with at least one nucleic acid molecule encoding the antibody disclosed herein; (b) expressing the nucleic acid molecule in said host cell; and (c) isolating said specific binding agent.

In certain embodiments, the disclosure relates to a method of inhibiting undesired ectodomain shedding in a mammal by administering a therapeutically effective amount of a specific binding agent disclosed herein to a subject in need thereof. In certain embodiments the specific binding agent is antibody mimetic, GPIbα affibody, or fragment thereof. Antibody mimetics or engineered affinity proteins are polypeptide based targeting moieties that can specifically bind to targets (in this case human GPIbα polypeptide Glu455-Phe478 (SEQ ID NO. 52) or GPIbα residues Lys461-Leu470 (SEQ ID NO. 53) or a fragment thereof) but are not specifically derived from antibody $V_H$ and $V_L$ sequences. Typically, a protein motif is recognized to be conserved among a number of proteins. One can artificially create libraries of these polypeptides with amino acid diversity and screen them for binding to targets (in this case human GPIbα Glu455-Phe478 (SEQ ID NO. 52) or GPIbα residues Lys461-Leu470 (SEQ ID NO. 53) or a fragment thereof) through phage, yeast, bacterial display systems, cell-free selections, and non-display systems. See Gronwall & Stahl, J Biotechnology, 2009, 140(3-4), 254-269. Antibody mimetics include affibody molecules, affilins, affitins, anticalins, avimers, darpins, fynomers, kunitz domain peptides, and monobodies.

In certain embodiments, the disclosure contemplates specific binding agents that are affibody molecules that bind the ADAM17 cleavage site in GPIbα, e.g., human GPIbα polypeptide Glu455-Phe478 (SEQ ID NO. 52) or GPIbα residues Lys461-Leu470 (SEQ ID NO. 53) or a fragment thereof. Affibody molecules are based on a protein domain derived from staphylococcal protein A (SPA). SPA protein domain denoted Z consists of three α-helices forming a bundle structure and binds the Fc portion of human IgG1. A combinatorial library may be created by varying surface exposed residues involved in the native interaction with Fc. Affinity proteins can be isolated from the library by phage display selection technology. See Orlova et al., Cancer Res., 2007, 67:2178-2186.

In certain embodiments, the disclosure contemplates specific binding agents that are monobodies that bind the ADAM17 cleavage site in GPIbα, e.g., human GPIbα polypeptide Glu455-Phe478 (SEQ ID NO. 52) or GPIbα residues Lys461-Leu470 (SEQ ID NO. 53) or a fragment thereof. Monobodies, sometimes referred to as Adnectins™, are antibody mimics based on the scaffold of the fibronectin type III domain (FN3). See Koide et al., Methods Mol. Biol. 2007, 352: 95-109. FN3 is a 10 kDa, β-sheet domain, that resembles the $V_H$ domain of an antibody with three distinct CDR-like loops, but lack disulfide bonds. FN3 libraries with randomized loops have successfully generated binders via phage display (M13 gene 3, gene 8; T7), mRNA display, yeast display and yeast two-hybrid systems. See Bloom & Calabro, Drug Discovery Today, 2009, 14(19-20):949-955.

In certain embodiments, the disclosure contemplates specific binding agents that are anticalins that bind the ADAM17 cleavage site in GPIbα, e.g., human GPIbα polypeptide Glu455-Phe478 (SEQ ID NO. 52) or GPIbα residues Lys461-Leu470 (SEQ ID NO. 53) or a fragment thereof. Anticalins, sometimes referred to as lipocalins, are a group of proteins characterized by a structurally conserved rigid β-barrel structure and four flexible loops. The variable loop structures form an entry to a ligand-binding cavity. Several libraries have been constructed based on natural human lipocalins, i.e., ApoD, NGAL, and Tlc. See Skerra, FEBS J., 275 (2008), pp. 2677-2683.

In certain embodiments, the disclosure contemplates specific binding agents that are ankyrin repeat (AR) proteins that bind the ADAM17 cleavage site in GPIbα, e.g., human GPIbα polypeptide Glu455-Phe478 (SEQ ID NO. 52) or GPIbα residues Lys461-Leu470 (SEQ ID NO. 53) or a fragment thereof. The ankyrin repeat (AR) protein is composed repeat domains consisting of a β-turn followed by two α-helices. Natural ankyrin repeat proteins normally consist of four to six repeats. The ankyrin repeats form a basis for DARPins™ (designed ankyrin repeat protein) which is a scaffold comprised of repeats of an artificial consensus ankyrin repeat domain. Combinatorial libraries have been created by randomizing residues in one repeat domain. Different numbers of the generated repeat modules can be connected together and flanked on each side by a capping repeat. The DARPin™ libraries are typically denoted NxC, where N stands for the N-terminal capping unit, C stands for the C-terminal capping domain and x for the number of library repeat domains, typically between two to four. Zahnd et al., J. Mol. Biol., 2007, 369:1015-1028.

In certain embodiments, the disclosure contemplates specific binding agents that are GPIbα peptide or nucleic acid aptamers that bind the ADAM17 cleavage site in GPIbα, e.g., human GPIbα polypeptide Glu455-Phe478 (SEQ ID NO. 52) or GPIbα residues Lys461-Leu470 (SEQ ID NO. 53) or a fragment thereof. Aptamers refer to affinity binding molecules identified from random proteins or nucleic acids libraries. Peptide aptamers have been selected from random loop libraries displayed on TrxA. See Borghouts et al., Expert Opin. Biol. Ther., 2005, 5:783-797. SELEX ("Systematic Evolution of Ligands by Exponential Enrichment") is a combinatorial chemistry technique for producing oligonucleotides of either single-stranded DNA or RNA that specifically bind to a target. Standard details on generating nucleic acid aptamers can be found in U.S. Pat. No. 5,475,096, and U.S. Pat. No. 5,270,163. The SELEX process provides a class of products which are referred to as nucleic acid ligands or aptamers, which has the property of binding specifically to a desired target compound or molecule. Each SELEX-identified nucleic acid ligand is a specific ligand of a given target compound or molecule. The SELEX process is based on the fact that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

Variants of Specific Binding Agents

Variants of Specific Binding Agents of the present disclosure include insertion, deletion, and/or substitution variants. In one aspect of the disclosure, insertion variants are provided wherein one or more amino acid residues supplement a specific binding agent amino acid sequence. Insertions may be located at either or both termini of the protein, or may be positioned within internal regions of the specific binding agent amino acid sequence. Insertion of variants with additional residues at either or both termini can include, for example, fusion proteins and proteins including amino acid tags or labels. Insertion variants include specific binding agent polypeptides wherein one or more amino acid residues are added to a specific binding agent amino acid sequence, or fragment thereof.

Variant products of the disclosure also include mature specific binding agent products. Such specific binding agent products have the leader or signal sequences removed, however the resulting protein has additional amino terminal residues. The additional amino terminal residues may be derived from another protein, or may include one or more residues that are not identifiable as being derived from a specific protein. Specific binding agent products with an additional methionine residue at position-1 (Met-1-specific binding agent) are contemplated, as are specific binding agent products with additional methionine and lysine residues at positions −2 and −1 (Met2-Lys-1-specific binding agent). Variants of specific binding agents having additional Met, Met-Lys, Lys residues (or one or more basic residues in general) are particularly useful for enhanced recombinant protein production in bacterial host cells.

The disclosure also embraces specific binding agent variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position-1 after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertion of variants also include fusion proteins as described above, wherein the amino and/or carboxy termini of the specific binding agent-polypeptide is fused to another polypeptide, a fragment thereof, or amino acid sequences which are not generally recognized to be part of any specific protein sequence.

In another aspect, the disclosure provides deletion variants wherein one or more amino acid residues in a specific binding agent polypeptide are removed. Deletions can be effected at one or both termini of the specific binding agent polypeptide, or from removal of one or more residues within the specific binding agent amino acid sequence. Deletion variants necessarily include all fragments of a specific binding agent polypeptide.

Antibody fragments include those portions of the antibody that bind to an epitope on the antigen polypeptide. Examples of such fragments include Fab and F(ab')2 fragments generated, for example, by enzymatic or chemical cleavage of full-length antibodies. Other binding fragments include those generated by recombinant DNA techniques, such as the expression of recombinant plasmids containing nucleic acid sequences encoding antibody variable regions. The disclosure also embraces polypeptide fragments of a GPIbα binding agent wherein the fragments maintain the ability to specifically bind a GPIbα polypeptide, e.g., cleavage site polypeptide. Fragments comprising at least 5, 10, 15, 20, 25, 30, 35, 40, 45 or 50 or more consecutive amino acids of a peptide or polypeptide of the disclosure are comprehended herein.

In still another aspect, the disclosure provides substitution variants of specific binding agents of the disclosure. Substitution variants are generally considered to be "similar" to the original polypeptide or to have a certain "percent identity" to the original polypeptide, and include those polypeptides wherein one or more amino acid residues of a polypeptide are removed and replaced with alternative residues. In one aspect, the substitutions are conservative in nature, however, the disclosure embraces substitutions that are also non-conservative.

Typical methods to determine the relatedness or percent identity of two polypeptides are designed to give the largest match between the sequences tested. Methods to determine identity are described in publicly available computer programs. Preferred computer program methods to determine identity between two sequences include, but are not limited to, the GCG program package, including GAP (Devereux et al., Nucl. Acid. Res., 12:387 (1984); Genetics Computer Group, University of Wisconsin, Madison, Wis., BLASTP, BLASTN, and FASTA (Altschul et al., J. Mol. Biol., 215: 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., Atlas of Protein Sequence and Structure, 5(3) (1978) for the PAM 250 comparison matrix; Henikoff et al., Proc. Natl. Acad. Sci. USA, 89:10915-10919 (1992) for the BLOSUM 62 comparison matrix) is also used by the algorithm.

In certain embodiments, the parameters for a polypeptide sequence comparison include the following:
Algorithm: Needleman et al., J. Mol. Biol., 48:443-453 (1970);
Comparison matrix: BLOSUM 62 from Henikoff et al., supra (1992);
Gap Penalty: 12
Gap Length Penalty: 4
Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence comparisons include the following:
Algorithm: Needleman et al., supra (1970); Comparison matrix: matches=+10, mismatch=0 Gap Penalty: 50 Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

As used herein, the twenty conventional amino acids and their abbreviations follow conventional usage. The amino acids may have either L or D stereochemistry (except for Gly, which is neither L nor D) and the polypeptides and compositions of the present disclosure may comprise a combination of stereochemistries. However, the L stereochemistry is typical. The disclosure also provides reverse molecules wherein the amino terminal to carboxy terminal sequence of the amino acids is reversed. For example, the reverse of a molecule having the normal sequence X1-X2-X3 would be X3-X2-X1. The disclosure also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty conventional amino acids, unnatural amino acids such as alpha-, alpha-disubstituted amino acids, N-alkyl amino acids, lactic acid, and other unconventional amino acids may also be suitable components for polypeptides of the present disclosure. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, sigma-N-methylarginine, and other similar amino acids and amino acids (e.g., 4-hydroxyproline).

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within 0.2 is included. In certain embodiments, those which are within 0.1 are included, and in certain embodiments, those within 0.5 are included.

The following hydrophilicity values have been assigned to these amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within 0.2 is included, in certain embodiments, those which are within 0.1 are included, and in certain embodiments, those within 0.5 are included. One may also identify epitopes from primary amino acid sequences on the basis of hydrophilicity. These regions are also referred to as "epitopic core regions."

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

Computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure.

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (5) confer or modify other functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence).

The specific binding agent molecules of this disclosure that are polypeptide or peptide substitution variants may have up to about ten to twelve percent of the original amino acid sequence replaced. For antibody variants, the heavy chain may have 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid replaced, while the light chain may have 25, 24, 23, 22, 21, 20, 19, 18, 17, 16, 15, 14, 13, 12, 11, 10, 9, 8, 7, 6, 5, 4, 3, 2, or 1 amino acid replaced.

Derivatives of Specific Binding Agents

The disclosure also provides derivatives of specific binding agent polypeptides. Derivatives include specific binding agent polypeptides bearing modifications other than insertion, deletion, or substitution of amino acid residues. Preferably, the modifications are covalent in nature, and include for example, chemical bonding with polymers, lipids, other organic, and inorganic moieties. Derivatives of the disclosure may be prepared to increase circulating half-life of a specific binding agent polypeptide, or may be designed to improve targeting capacity for the polypeptide to desired cells, tissues, or organs.

The disclosure further embraces derivative binding agents covalently modified to include one or more water soluble polymer attachments such as polyethylene glycol, polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are specific binding agent products covalently modified with polyethylene glycol (PEG) subunits. Water-soluble polymers may be bonded at specific positions, for example at the amino terminus of the specific binding agent products, or randomly attached to one or more side chains of the polypeptide. The use of PEG for improving the therapeutic capacity for specific binding agent, and for humanized antibodies in particular, is described in U.S. Pat. No. 6,133,426.

Target Sites for Antibody Mutagenesis

Certain strategies can be employed to manipulate inherent properties of a GPIbα specific antibody, such as the affinity of the antibody for its target. These strategies include the use of site-specific or random mutagenesis of the polynucleotide molecule encoding the antibody to generate antibody variants, followed by a screening step designed to recover antibody variants that exhibit the desired change, e.g. increased or decreased affinity.

The amino acid residues most commonly targeted in mutagenic strategies are those in the CDRs. As described supra, these regions contain the residues that actually interact with GPIbα and other amino acids that affect the spatial arrangement of these residues. However, amino acids in the framework regions of the variable domains outside the CDR regions have also been shown to make contributions to the antigen-binding properties of the antibody, and can be targeted to manipulate such properties.

Smaller and more effectively screened libraries of antibody variants can be produced by restricting random or site-directed mutagenesis to sites in the CDRs that correspond to areas prone to "hyper-mutation" during the somatic affinity maturation process. See Chowdhury and Pastan, Nature Biotech, 17: 568-572 [1999] and references therein. The types of DNA elements known to define hyper-mutation sites in this manner include direct and inverted repeats, certain consensus sequences, secondary structures, and palindromes. The consensus DNA sequences include the tetra-base sequence Purine-G-Pyrimidine-A/T (i.e. A or G-G-C or T-A or T) and the serine codon AGY (wherein Y can be a C or a T).

Thus, an embodiment of the present disclosure includes mutagenic strategies with the goal of increasing the affinity of an antibody for its target. These strategies include mutagenesis of the entire variable heavy and light chain, mutagenesis of the CDR regions only, mutagenesis of the consensus hypermutation sites within the CDRs, mutagenesis of framework regions, or any combination of these approaches ("mutagenesis" in this context could be random or site-directed). Definitive delineation of the CDR regions and identification of residues comprising the binding site of an antibody can be accomplished though solving the structure of the antibody in question, and the antibody-ligand complex, through techniques known to those skilled in the art, such as X-ray crystallography. Various methods based on analysis and characterization of such antibody crystal structures are known to those of skill in the art and can be employed, although not definitive, to approximate the CDR regions. Examples of such commonly used methods include the Kabat, Chothia, AbM and contact definitions.

The Kabat definition is based on the sequence variability and is the most commonly used definition to predict CDR regions. The Chothia definition is based on the location of the structural loop regions. The AbM definition is a compromise between the Kabat and Chothia definition. AbM is an integral suite of programs for antibody structure modeling produced by Oxford Molecular Group. The AbM suite models the tertiary structure of an antibody from primary sequencing using a combination of knowledge databases and ab initio methods.

By convention, the CDR regions in the heavy chain are typically referred to as H1, H2 and H3 and are numbered sequentially in order counting from the amino terminus to the carboxy terminus. The CDR regions in the light chain are typically referred to as L1, L2 and L3 and are numbered sequentially in order counting from the amino terminus to the carboxy terminus.

The CDR-H1 is approximately 10 to 12 residues in length and typically starts 4 residues after a Cys according to the Chothia and AbM definitions or typically 5 residues later according to the Kabat definition. The H1 is typically followed by a Trp, typically Trp-Val, but also Trp-Ile, or Trp-Ala. The length of H1 is approximately 10 to 12 residues according to the AbM definition while the Chothia definition excludes the last 4 residues.

The CDR-H2 typically starts 15 residues after the end of H1 according to the Kabat and AbM definition. The residues preceding H2 are typically Leu-Glu-Trp-Ile-Gly but there are a number of variations. H2 is typically followed by the amino acid sequence Lys/Arg-Leu/Ile/Val/Phe/Thr/Ala-Thr/Ser/Ile/Ala. According to the Kabat definition, the length of the H2 is approximately 16 to 19 residues where the AbM definition predicts the length to be typically 9 to 12 residues.

The CDR-H3 typically starts 33 residues after the end of H2 and is typically preceded by the amino acid sequence (typically Cys-Ala-Arg). The H3 is typically followed by the amino acid sequence-Gly. The length of H3 can be anywhere between 3 to 25 residues.

The CDR-L1 typically starts at approximately residue 24 and will typically follow a Cys. The residue after the CDR-L1 is always a Trp and will typically begin the sequence Trp-Tyr-Gln, Trp-Leu-Gln, Trp-Phe-Gln, or Trp-Tyr-Leu. The length of CDR-L1 is approximately 10 to 17 residues. The punitive CDR-L1 for the antibodies of the disclosure follows this pattern exactly with a Cys residue followed by 15 amino acids then Trp-Tyr-Gln.

The CDR-L2 starts approximately 16 residues after the end of L1. It will generally follow residues Ile-Tyr, Val-Tyr, Ile-Lys or Ile-Phe. The length of CDR-L2 is approximately 7 residues.

The CDR-L3 typically starts 33 residues after the end of L2 and typically follows a Cys. L3 is typically followed by the amino acid sequence Phe-Gly-XXX-Gly (SEQ ID NO: 51). The length of L3 is approximately 7 to 11 residues.

Various methods for modifying antibodies have been described in the art. Each humanized immunoglobulin chain will usually comprise, in addition to the CDRs, amino acids from the donor immunoglobulin framework that are, e.g., capable of interacting with the CDRs to affect binding affinity, such as one or more amino acids which are immediately adjacent to a CDR in the donor immunoglobulin or those within about 3 angstroms as predicted by molecular modeling. The heavy and light chains may each be designed by using any one or all of various position criteria. When combined into an intact antibody, the humanized immunoglobulins of the present disclosure will be substantially non-immunogenic in humans and retain substantially the same affinity as the donor immunoglobulin to the antigen, such as a protein or other compound containing an epitope.

Humanized antibodies are obtained by chain shuffling, using, for example, phage display technology, and a polypeptide comprising a heavy or light chain variable domain of a non-human antibody specific for an antigen of interest is combined with a repertoire of human complementary (light or heavy) chain variable domains. Hybrid pairings that are specific for the antigen of interest are identified and human chains from the selected pairings are combined with a repertoire of human complementary variable domains (heavy or light). In another embodiment, a component of a CDR from a non-human antibody is combined with a repertoire of component parts of CDRs from human antibodies. From the resulting library of antibody polypeptide dimers, hybrids are selected and used in a second humanizing shuffling step. Alternatively, this second step is eliminated if the hybrid is already of sufficient human character to be of therapeutic value.

U.S. Pat. Nos. 8,293,235, 7,262,050, 7,241,877, 7,022,500, 6,982,321, 6,639,055, and 6,054,297 describes methods for making humanized antibodies by substituting a CDR amino acid sequence for the corresponding human CDR amino acid sequence and/or substituting a FR amino acid sequence for the corresponding human FR amino acid sequences. These sequences can be used as a source of human sequence, e.g., for framework regions and CDRs. See e.g., U.S. Pat. Nos. 6,300,064 and 8,513,164.

Modification of an antibody by any of the methods known in the art is typically designed to achieve increased binding affinity for an antigen and/or reduce immunogenicity of the antibody in the recipient. In one approach, humanized antibodies can be modified to eliminate glycosylation sites in order to increase affinity of the antibody for its cognate antigen. Techniques such as "reshaping," "hyperchimerization," and "veneering/resurfacing" have produced humanized antibodies with greater therapeutic potential. U.S. Pat. No. 6,072,035 to Hardman et al., issued Jun. 6, 2000, which describes methods for reshaping antibodies. While these techniques diminish antibody immunogenicity by reducing the number of foreign residues, they do not prevent anti-idiotypic and anti-allotypic responses following repeated administration of the antibodies.

In certain instances, humanizing antibodies result in a loss of antigen binding capacity. It is therefore preferable to "back mutate" the humanized antibody to include one or more of the amino acid residues found in the original (most often rodent) antibody in an attempt to restore binding affinity of the antibody.

Non-Peptide Specific Binding Agent Analogs/Protein Mimetics

Furthermore, nonpeptide specific binding agent analogs of peptides that provide a stabilized structure or lessened bio-degradation, are also contemplated. Specific binding agent peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation which retains the ability to recognize and bind GPIbα or cleavage site. In one aspect, the resulting analog/mimetic exhibits increased binding affinity for GPIbα.

If desired, the specific binding agent peptides of the disclosure can be modified, for instance, by glycosylation, amidation, carboxylation, or phosphorylation, or by the creation of acid addition salts, amides, esters, in particular C-terminal esters, and N-acyl derivatives of the peptides of the disclosure. The specific binding agent peptides also can be modified to create peptide derivatives by forming covalent or noncovalent complexes with other moieties. Covalently-bound complexes can be prepared by linking the chemical moieties to functional groups on the side chains of amino acids comprising the specific binding agent peptides, or at the N- or C-terminus.

In particular, it is anticipated that the specific binding agent peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The disclosure accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. Any of the peptides of the present disclosure may comprise one, two, or more of any of these labels.

Methods of Making Specific Binding Agents

Specific binding agents of the present disclosure that are proteins can be prepared by chemical synthesis in solution or on a solid support in accordance with conventional techniques. The current limit for solid phase synthesis is about 85-100 amino acids in length. However, chemical synthesis techniques can often be used to chemically ligate a series of smaller peptides to generate full length polypeptides. Various automatic synthesizers are commercially available and can be used in accordance with known protocols.

Solid phase peptide synthesis methods use a copoly (styrene-divinylbenzene) containing 0.1-1.0 mM amines/g polymer. These methods for peptide synthesis use butyloxycarbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide. On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hour at 0 degree C.). After evaporation of the reagents, the specific binding agent peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous specific binding agent peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Chemical synthesis of anti-GPIbα antibodies, derivatives, variants, and fragments thereof, as well as other protein-based GPIbα binding agents permits incorporation of non-naturally occurring amino acids into the agent.

Recombinant DNA techniques are a convenient method for preparing full length antibodies and other large proteinaceous specific binding agents of the present disclosure, or fragments thereof. A cDNA molecule encoding the antibody or fragment may be inserted into an expression vector, which can in turn be inserted into a host cell for production of the antibody or fragment. It is understood that the cDNAs encoding such antibodies may be modified to vary from the "original" cDNA (translated from the mRNA) to provide for codon degeneracy or to permit codon preference usage in various host cells.

Generally, a DNA molecule encoding an antibody can be obtained using procedures described herein in the Examples. Where it is desirable to obtain Fab molecules or CDRs that are related to the original antibody molecule, one can screen a suitable library (phage display library; lymphocyte library, etc.) using standard techniques to identify and clone related Fabs/CDRs. Probes used for such screening may be full length or truncated Fab probes encoding the Fab portion of the original antibody, probes against one or more CDRs from the Fab portion of the original antibody, or other suitable probes. After hybridization, the probed blot can be washed at a suitable stringency, depending on such factors as probe size, expected homology of probe to clone, the type of library being screened, and the number of clones being screened. Examples of high stringency screening are 0.1 times SSC, and 0.1 percent SDS at a temperature between 50-65 degree C.

A variety of expression vector/host systems may be utilized to contain and express the polynucleotide molecules encoding the specific binding agent polypeptides of the disclosure. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

Mammalian cells that are useful in recombinant specific binding agent protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells, as well as hybridoma cell lines as described herein. Mammalian cells are preferred for preparation of those specific binding agents such as antibodies and antibody fragments that are typically glycosylated and require proper refolding for activity. Preferred mammalian cells include CHO cells, hybridoma cells, and myeloid cells.

Where recombinant specific binding agent protein is expressed without a leader or transport sequence, it may include an amino terminal methionine residue. This residue may or may not be subsequently cleaved from the expressed recombinant protein to provide a final specific binding agent product.

For example, the specific binding agents may be recombinantly expressed in yeast using a commercially available expression system, e.g., the *Pichia* Expression System™ (Invitrogen™ San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted specific binding agent peptide is purified from the yeast growth medium by, e.g., the methods used to purify the peptide from bacterial and mammalian cell supernatants.

Alternatively, the cDNA encoding the specific binding agent peptide may be cloned into the baculovirus expression vector pVL1393 (PharMingen™, San Diego, Calif.). This vector can be used according to the manufacturer's directions (PharMingen™) to infect *Spodoptera frugiperda* cells in sF9 protein-free media and to produce recombinant protein. The specific binding agent protein can be purified and concentrated from the media using a heparin-Sepharose column (Pharmacia™).

Alternatively, the peptide may be expressed in an insect system. Insect systems for protein expression are well known to those of skill in the art. In one such system,

*Autographa californica* nuclear polyhedrosis virus (AcNPV) can be used as a vector to express foreign genes in *Spodoptera frugiperda* cells or in *Trichoplusia* larvae. The specific binding agent peptide coding sequence can be cloned into a nonessential region of the virus, such as the polyhedrin gene, and placed under control of the polyhedrin promoter. Successful insertion of the specific binding agent peptide will render the polyhedrin gene inactive and produce recombinant virus lacking coat protein coat.

In another example, the DNA sequence encoding the specific binding agent peptide can be amplified by PCR and cloned into an appropriate vector for example, pGEX-3X (Pharmacia™). The pGEX vector is designed to produce a fusion protein comprising glutathione-S-transferase (GST), encoded by the vector, and a specific binding agent protein encoded by a DNA fragment inserted into the vector's cloning site. The primers for the PCR can be generated to include for example, an appropriate cleavage site. Where the specific binding agent fusion moiety is used solely to facilitate expression or is otherwise not desirable as an attachment to the peptide of interest, the recombinant specific binding agent fusion protein may then be cleaved from the GST portion of the fusion protein. The pGEX-3X/specific binding agent peptide construct is transformed into *E. coli* XL-1 Blue cells (Stratagene™, La Jolla Calif.), and individual transformants isolated and grown. Plasmid DNA from individual transformants can be purified and partially sequenced using an automated sequencer to confirm the presence of the desired specific binding agent encoding nucleic acid insert in the proper orientation.

Expression of polynucleotides encoding anti-GPIbα antibodies and fragments thereof using the recombinant systems described above may result in production of antibodies or fragments thereof that must be "re-folded" (to properly create various disulphide bridges) in order to be biologically active. Typical refolding procedures for such antibodies are set forth in the Examples herein and in the following section.

Specific binding agents made in bacterial cells may be produced as an insoluble inclusion body in the bacteria, can be purified as follows. Host cells can be sacrificed by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000.times.g. The specific binding agent-containing pellet can be resuspended in 50 mM Tris, pH 8, and 10 mM EDTA, layered over 50% glycerol, and centrifuged for 30 min. at 6000 times g. The pellet can be resuspended in standard phosphate buffered saline solution (PBS) free of Mg and Ca. The specific binding agent can be further purified by fractionating the resuspended pellet in a denaturing SDS polyacrylamide gel (Sambrook et al., supra). The gel can be soaked in 0.4 M KCl to visualize the protein, which can be excised and electroeluted in gel-running buffer lacking SDS. If the GST fusion protein is produced in bacteria, as a soluble protein, it can be purified using the GST Purification Module™ (Pharmacia™).

Host cell strains can be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, WI38, as well as hybridoma cell lines, and the like have specific cellular machinery and characteristic mechanisms for such post-translational activities and can be chosen to ensure the correct modification and processing of the introduced, foreign protein.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for DHFR which confers resistance to methotrexate; gpt which confers resistance to mycophenolic acid; neo which confers resistance to the aminoglycoside G418 and confers resistance to chlorsulfuron; and hygro which that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

Purification and Refolding of Specific Binding Agents

In some cases, the specific binding agents produced using procedures described above may need to be "refolded" and oxidized into a proper tertiary structure and generating di-sulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

It will be desirable to purify specific binding agent proteins or variants thereof of the present disclosure. Protein purification techniques are well known to those of skill in the art. These techniques involve, at one level, the crude fractionation of the polypeptide and non-polypeptide fractions. Having separated the specific binding agent polypeptide from other proteins, the polypeptide of interest can be further purified using chromatographic and electrophoretic techniques to achieve partial or complete purification (or purification to homogeneity). Analytical methods particularly suited to the preparation of a pure specific binding agent peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concerns the purification, and in particular embodiments, the substantial purification, of an encoded specific binding agent protein or peptide. The term "purified specific binding agent protein or peptide" as used herein, is intended to refer to a composition, isolatable from other components, wherein the specific binding agent protein or peptide is purified to any degree relative to its naturally-obtainable state. A purified specific binding agent protein or peptide therefore also refers to a specific binding agent protein or peptide, free from the environment in which it may naturally occur.

Generally, "purified" will refer to a specific binding agent composition that has been subjected to fractionation to remove various other components, and which composition substantially retains its expressed biological activity. Where the term "substantially purified" is used, this designation will refer to a specific binding agent composition in which the specific binding agent protein or peptide forms the major component of the composition, such as constituting about 50%, about 60%, about 70%, about 80%, about 90%, about 95% or more of the proteins in the composition.

Various methods for quantifying the degree of purification of the specific binding agent will be known to those of skill in the art in light of the present disclosure. These include, for example, determining the specific binding activity of an active fraction, or assessing the amount of specific binding agent polypeptides within a fraction by SDS/PAGE analysis. A preferred method for assessing the purity of a specific binding agent fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the expressed specific binding agent protein or peptide exhibits a detectable binding activity.

Various techniques suitable for use in specific binding agent protein purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified specific binding agent.

There is no general requirement that the specific binding agent always be provided in its most purified state. Indeed, it is contemplated that less substantially specific binding agent products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of specific binding agent protein product, or in maintaining binding activity of an expressed specific binding agent protein.

Binding Assays

Immunological binding assays typically utilize a capture agent to bind specifically to and often immobilize the analyte target antigen. The capture agent is a moiety that specifically binds to the analyte. In one embodiment of the present disclosure, the capture agent is an antibody or fragment thereof that specifically binds GPIbα or the ectodomain cleave site.

Immunological binding assays frequently utilize a labeling agent that will signal the existence of the bound complex formed by the capture agent and antigen. The labeling agent can be one of the molecules comprising the bound complex; i.e. it can be labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

Immunological binding assays can be of the non-competitive type. These assays have an amount of captured analyte that is directly measured. For example, in one preferred "sandwich" assay, the capture agent (antibody) can be bound directly to a solid substrate where it is immobilized. These immobilized antibodies then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin.

Immunological binding assays can be of the competitive type. The amount of analyte present in the sample is measure indirectly by measuring the amount of an added analyte displaced, or competed away, from a capture agent by the analyte present in the sample. In one preferred competitive binding assay, a known amount of analyte, usually labeled, is added to the sample and the sample is then contacted with an antibody (the capture agent). The amount of labeled analyze bound to the antibody is inversely proportional to the concentration of analyte present in the sample.

In another preferred competitive binding assay, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

The competitive binding assays can be used for cross-reactivity determinations to permit a skilled artisan to determine if a protein or enzyme complex which is recognized by a specific binding agent of the disclosure is the desired protein and not a cross-reacting molecule or to determine whether the antibody is specific for the antigen and does not bind unrelated antigens. In assays of this type, antigen can be immobilized to a solid support and an unknown protein mixture is added to the assay, which will compete with the binding of the specific binding agents to the immobilized protein. The competing molecule also binds one or more antigens unrelated to the antigen. The ability of the proteins to compete with the binding of the specific binding agents antibodies to the immobilized antigen is compared to the binding by the same protein that was immobilized to the solid support to determine the cross-reactivity of the protein mix.

The present disclosure also provides Western blot methods to detect or quantify the presence of GPIbα in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or fragments thereof that specifically bind GPIbα and the resulting complex is detected. These antibodies may be directly labeled or alternatively may be subsequently detected using labeled antibodies that specifically bind to the antibody.

Pharmaceutical Compositions

Pharmaceutical compositions of GPIbα specific binding agents or antibodies are within the scope of the present disclosure. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of a specific binding agent, such as an antibody, or a fragment, variant, derivative or fusion thereof as described herein, in admixture with a pharmaceutically acceptable agent. In a preferred embodiment, pharmaceutical compositions comprise antagonist specific binding agents that prevents GPIbα shedding in admixture with a pharmaceutically acceptable agent. Typically, the specific binding agents will be sufficiently purified for administration to an animal The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The optimal pharmaceutical composition will be determined by one skilled in the art depending upon, for example, the intended route of administration, delivery format, and desired dosage. Such compositions may influence the physical state, stability, rate of in vivo release, and rate of in vivo clearance of the specific binding agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present disclosure, binding agent compositions may be prepared for storage by mixing the selected composition having the desired degree of purity with optional formulation agents in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this disclosure may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized.

It is also contemplated that certain formulations may be administered orally. In one embodiment of the present disclosure, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate (Langer et al., supra) or poly-D(−)-3-hydroxybutyric acid. Sustained-release compositions also include liposomes, which can be prepared by any of several methods known in the art.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present disclosure is directed to kits for producing a single-dose administration unit. The kits may each contain both a first container having a dried protein and a second container having an aqueous formulation. Also included within the scope of this disclosure are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent which is a polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semipermeable polymeric enclosures or membranes that allow the release of the protein product(s) but prevent the destruction of the cells by the patient's immune system or by other detrimental factors from the surrounding tissues.

EXAMPLES

Materials and Methods

Materials and animals—Immunization of C57BL mice and production of mAbs against GPIbα were carried out by Green Mountain Antibodies™ (Burlington, Vt., USA). CCCP, L-cysteine, and BSA were obtained from Sigma-Aldrich™ (St. Louis, Mo., USA). GM6001, W7, and PMA were from Calbiochem™ (La Jolla, Calif., USA). The anti-GPV mAb SW16 was purchased from Santa Cruz Biotechnology™ (Santa Cruz, Calif., USA). Biotinylated antibody was prepared using sulfo-N hydroxysuccinimide-biotin (Thermo Scientific™, Rockford, Ill., USA) and following the manufacturer's instruction. C57BL/6J mice (designated WT), mice expressing a variant GPIbα subunit where most of the extracellular domain of GPIbα has been replaced by an isolated domain of the IL-4 receptor fused to the transmembrane and cytoplasmic residues of GPIbα (IL4Tg) and mice expressing a wild-type human GPIbα transgene in the absence of mouse GPIbα (hTg).

Preparation of washed human platelets—Human whole blood was obtained from healthy human volunteers. Platelet-rich plasma (PRP) was isolated by centrifugation at 140×g. Then 10 mL of PIPES-buffered saline with prostaglandin E1 (1 µmol L-1) was mixed with PRP followed by centrifugation at 1900×g for 8 min. The platelet pellet was resuspended in a modified Tyrode's buffer without calcium containing (in mmol $L^{-1}$) NaCl 134, Na2HPO4 0.34, KCl 2.9, MgCl2 1, glucose 5, NaHCO3 12, HEPES 20, pH 7.35. Platelet counts were measured using a HemaTrue™ hematology analyzer (HESKA™, Loveland, Colo., USA).

Preparation of Fab fragment—Purified mAb (10 mg mL 1 in PBS) was incubated with immobilized papain (Thermo Scientific™) in the presence of 20 mmol $L^{-1}$ L-Cysteine at 37° C. overnight. After papain was removed via centrifugation, the generated Fab fragment was purified using Protein A beads (Invitrogen™, Carlsbad, Calif., USA). Binding of mAbs to synthetic peptide and purified GPIb-IX Human GPIb-IX complex was purified as reported in Yan et al., Biochemistry, 2011, 50: 10598-606, from outdated and deidentified leukoreduced apheresis derived platelets obtained from Blood and Tissue Services at Children's Healthcare of Atlanta™. Synthetic peptides (New England Peptide™, Gardner, Mass., USA) and purified GPIb-IX in PBS (both 6 µg mL-1) were immobilized in separate microtiter wells (Costar 3690; Corning™ Inc, Corning, N.Y., USA) at 4° C. overnight. After incubation in the blocking buffer (20 mmol $L^{-1}$ HEPES, 0.2 mol $L^{-1}$ NaCl, 0.05%

Tween-20, 2% BSA, pH 7.4) at room temperature (RT) for 2 h, different doses of normal mouse IgG or purified mAb dissolved in the blocking buffer were added to the wells and incubated for 1 h. The wells were then washed three times with the blocking buffer without BSA and incubated for an additional 1 h with biotinylated goat anti-mouse IgG (1:50 in the blocking buffer). After three washes, the wells were incubated for 1 h with streptavidin alkaline phosphatase (1:2000 in the blocking buffer). After three washes, bound antibodies were quantified by adding the alkaline phosphatase substrate (Bio-Rad™, Hercules, Calif., USA) and recording the optical density at 405 nm in a SpectraMax Plus™ microplate reader (Spectramax Molecular Devices™, Sunnyvale, Calif., USA).

Expression and purification of green fluorescent protein-lactadherin C2 domain (GFP-Lact-C2)—The DNA fragment encoding the green fluorescent protein (GFP)-lactadherin (Lact)-C2 fusion protein was amplified from the pEGFP-Lact-C2 plasmid (Addgene™, Cambridge, Mass., USA). The fragment was further appended with a fragment encoding the hexahistidine tag by another round of PCR. The product was ligated in the pET-22b(+) vector (Novagen™, Madison, Wis., USA) as an NdeI/EcoRI fragment and transformed into Escherichia coli BL21(DE3) cells. Purified protein was dialyzed extensively against 50 mmol $L^{-1}$ Tris, 150 mmol $L^{-1}$ NaCl, pH 7.4, before being stored at 80° C. The protein concentration was determined using the molar extinction coefficient of 55 000 mol $L^{-1}$ $cm^{-1}$ at 480 nm.

Western blot—Washed human platelets ($1.2 \times 10^7$ cells mL-1) in modified Tyrode's buffer containing 2.1 mmol $L^{-1}$ $CaCl_2$ were incubated with 150 µmol $L^{-1}$ W7 or 100 µmol $L^{-1}$ CCCP for 2 h. The proteins were resolved in an 8% Bis-Tris SDS gel under reducing conditions, transferred to PVDF membranes, and blotted with WM23 (for glycocalicin and GPIbα), 6B12 (GPVI), and anti-actin antibody.

Platelet aggregometry—Agonist-induced platelet aggregation was monitored in a dual-channel Chrono-Log aggregometer (Havertown™, PA, USA). PRP was prepared via centrifugation of whole blood at 170×g for 15 min. Autologous PPP was prepared via centrifugation (after removal of PRP) at 2400×g for 20 min and used to adjust the final platelet count in PRP to $2.5 \times 10^8$ cells $mL^1$. Aggregation was initiated in 250 µL of stirred PRP by the addition of noted agonists. When required, the antibody was added to PRP and incubated for at least 5 min before stimulation with agonists.

Generation of mAbs Targeting the Shedding Cleavage Site in Human GPIbα

Figure 1A:
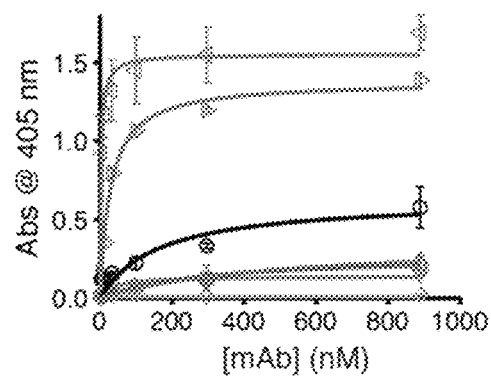
FIG. 1A shows data on the binding of selected monoclonal antibodies (mAbs) to purified human glycoprotein (GP) Ib-IX.
Figure 1B:
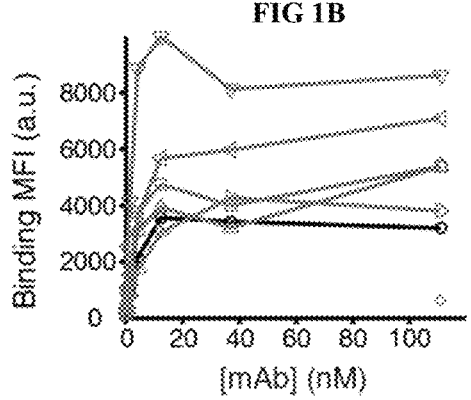
FIG. 1B shows data on the binding of selected monoclonal antibodies (mAbs) to washed human platelets.

If a reagent is to inhibit shedding of GPIbα but not that of any other receptor, it needs to act directly on GPIbα, the shedding substrate, rather than on ADAM17, the sheddase. One way to achieve substrate specific shedding inhibition was to bind the shedding substrate with sufficient binding affinity such as to block its access to the sheddase. Therefore, an antibody targeting the sequence flanking the shedding cleavage site in human GPIbα could inhibit its shedding. A synthetic peptide that corresponds to human GPIbα sequence Glu455-Phe478 (SEQ ID NO. 52) was used as the antigen for mouse immunization. Hybridoma clones obtained from immunized mice were screened in ELISAs for binding activities to the ovalbumin-conjugated antigen peptide and shorter shedding-site peptide that corresponded to GPIbα residues Lys461-Leu470 (SEQ ID NO. 53). Positive clones were further screened for their abilities to bind purified human GPIb-IX complex by ELISA and to inhibit W7-induced GPIbα shedding in human platelets through flow cytometry. In the end, six positive single clones were selected to produce mAbs. All six purified mAbs exhibited strong binding to washed human platelets, but they bound to immobilized GPIb-IX to varying degrees (FIG. 1A,B). Two mAbs, 5G6 and 15C6, with the fitted Kd of 3.29 and 28.18 nmol $L^{-1}$, respectively, showed much higher affinities for GPIb-IX than the other four. It is noteworthy, however, that the other four mAbs displayed higher binding than the negative control, suggesting that their binding affinity for GPIb-IX may be weaker and beyond the detection range in our ELISA. Further characterization revealed that these mAbs exhibited strong binding to multivalent ovalbumin-conjugated shedding-site peptide but disparate binding to the monovalent shedding-site peptide that was directly immobilized in the microtiter plate (FIG. 1C,D). Clone 5G6 binding of multivalent shedding-site peptide was similar to its binding to washed platelets, suggesting that mAbs bind GPIbα in human platelets via multivalent binding, supported by the high expression level of GPIbα in platelets and the bivalent structure of a mAb.

Clone 5G6 Binds Specifically to the Shedding Cleavage Site of Human GPIbα in Platelets With the lowest Kd for GPIb-IX, mAb 5G6 was henceforth characterized in detail. Whether 5G6 specifically recognizes the shedding cleavage site of human GPIbα in platelets was examined first. Like WM23, an anti-GPIbα mAb reported in Berndt et al., 5G6 exhibited strong binding to fresh human platelets as detected by flow cytometry using FITC-conjugated goat anti-mouse IgG (FIGS. 2A and 1B). The binding reached saturation at 12 and 36 nmol $L^{-1}$ for 5G6 and its Fab fragments, respectively (FIG. 2B,C). The binding affinity of 5G6 for human platelet was similar to that obtained using the purified GPIb-IX complex (FIG. 2C). Moreover, immunoblotting of platelet lysate with 5G6 produced essentially the same protein bands as those blotted with WM23 (FIG. 2D), indicating that 5G6 specifically recognizes GPIbα. Finally, premixing the shedding-site peptide blocked binding of 5G6 to human platelets, confirming that the 5G6 epitope is located at the shedding cleavage site of GPIbα (FIG. 2E).

The sequence flanking the GPIbα shedding cleavage site is not conserved across species. Only two residues are conserved between human GPIbα Lys461-Leu470 (SEQ ID NO. 53) and its murine counterpart sequence. Since 5G6 was raised to recognize the shedding cleavage site in human GPIbα, it did not, as expected, bind either wild-type murine platelets or those expressing a mutant GPIbα in which its extracellular domain was replaced by that of interleukin-4 receptor a (IL4Tg). Instead, it bound transgenic murine platelets expressing only human GPIbα (hTg; FIG. 2F), confirming that 5G6 was directed against the shedding cleavage site of human GPIbα, not mouse GPIbα, or any other receptors in the platelet.

Clone 5G6 Inhibits Specifically GPIbα Shedding in Human Platelets

To address whether 5G6 inhibits GPIbα shedding, WM23 was used to monitor the level of GPIbα on the platelet surface and the amount of glycocalicin released from the platelet after incubation of fresh human platelets with 5G6. Since both 5G6 and WM23 are of mouse origin, biotin-labeled WM23 and FITC-conjugated streptavidin were used for GPIbα detection by flow cytometry. W7 or CCCP was added to induce GPIbα shedding in platelets. Incubation of washed platelets with 5G6 or its Fab fragment at the saturating concentration inhibited not only constitutive but also W7- or CCCP-induced down-regulation of GPIbα expression on the platelet surface (FIG. 3A). The extent of inhibition was comparable to that by GM6001. Consistently, immunoblotting of the platelet lysate and supernatant showed that both 5G6 and its Fab fragment inhibited W7- and CCCP-induced decrease of GPIbα in human platelets and concurrent increase of glycocalicin released into the supernatant (FIG. 3B). Overall, these results demonstrated that 5G6 as well as its Fab fragment could inhibit GPIbα shedding in human platelets.

To address the specificity of 5G6 inhibition of GPIbα shedding, the effect of 5G6 treatment on the shedding of GPVI and GPV in human platelets was tested. Since anti-GPVI mAb 6B12 does not work well in flow cytometry and anti-GPV mAb SW16 is not amenable to Western blot, shedding of GPVI and GPV were monitored by Western blot and flow cytometry, respectively. FIG. 4A shows that W7-induced GPVI shedding was significantly inhibited by GM6001 but not 5G6 or its Fab fragment. Since SW16 is a mouse antibody, human platelets were preincubated with only 36 nmol $L^{-1}$ 5G6 Fab before shedding stimulation. FIG. 4B shows that GPV was downregulated by W7 or PMA stimulation, which was inhibited by GM6001. But 5G6 Fab fragment did not inhibit W7- or PMA-induced GPV shedding. Overall, these results demonstrated the substrate specificity of 5G6 inhibition.

Clone 5G6 does not Affect Platelet Activation and Aggregation

Many, but not all, antibodies targeting the extracellular domain of GPIbα cause platelet activation or have pathogenic effects on platelets, although the underlying mechanisms remain to be defined. Experiments were performed to establish whether 5G6 affects platelet activation or causes platelet apoptosis. The addition of 5G6 to PRP did not induce aggregation (FIG. 5A). Nor did it significantly affect the aggregation induced by ristocetin (FIG. 5A), suggesting that 5G6 does not impact GPIbα association with von Willebrand factor. At the molecular level, treatment of washed platelets with 5G6 did not induce activation of integrin aIIbb3 or increase the expression of P-selectin (FIG. 5B). Unlike ionomycin, 5G6 did not cause the exposure of phosphotidylserine (FIG. 5B). Overall, these results indicated that 5G6 has no detectable effect on platelet activation and aggregation.

Fully Human Monoclonal Antibodies (mAbs) to Human GPIbα

One generates fully human mAbs from nonhuman variable regions using information from the human germline repertoire. Residues within and proximal to CDRs and the VH/VL interface (e.g., SEQ ID NOs 18-43) are iteratively explored substitutions to the closest human germline sequences using semi-automated computational methods. See Bernett et al., J Mol. Biology, 2010, 396(5):1474-1490, hereby incorporated by reference in entirety. One generates fully human antibodies with substitutions compared to the parent murine sequences. Substitutions may be in the CDRs.

The engineering process to generate fully human mAbs from murine Fvs consists of five main steps: (1) design of framework-optimized VH and VL template sequences, (SEQ ID NOs: 1-16) (2) identification of the closest matching human germline sequence for the framework-optimized VH and VL, (3) screening of all possible single substitutions that increase the sequence identity of the framework-optimized sequence to the closest human germline sequence, (4) screening of VH and VL variants consisting of combinations of neutral or affinity enhancing single substitutions, and (5) screening of the highest-affinity VH and VL pairs to generate the final fully human mAb.

One defines two principal scores used to measure sequence humanness. Human identity is defined as the number of exact sequence matches between the Fv and the highest identity human germline VH, Vκ, JH, and Jκ chains (the D-segment for the heavy chain is not included). The second score is the number of total "human 9-mers", which is an exact count of 9-mer stretches in the Fv that perfectly match any one of the corresponding stretches of nine amino acids in our set of functional human germline sequences. Both human 9-mers and human identity are expressed as percentages throughout in order to enable comparison between antibody Fvs of different lengths.

The invention claimed is:

1. An anti-glycoprotein (GP)Ibα monoclonal antibody, humanized monoclonal antibody, chimeric antibody, or antigen binding fragment thereof, comprising a) a variable heavy chain ($V_H$) region comprising three heavy chain complementarity determining regions (CDRs) and b) a variable light chain ($V_L$) region comprising three light chain CDRs,
wherein the three light chain CDRs are:
light chain CDR1: RASGNIYNYLA (SEQ ID NO. 34);
light chain CDR2: NAKTLAD (SEQ ID NO. 39); and
light chain CDR3: QHFWDTPWT (SEQ ID NO. 42);
wherein the three heavy chain CDRs are:
heavy chain CDR1: TSNMGVV (SEQ ID NO. 21);
heavy chain CDR2: HILWNDGKFYNPALKS (SEQ ID NO. 24); and
heavy chain CDR3: LFTTTTSGYFDV (SEQ ID NO. 28),
and wherein the monoclonal antibody, humanized monoclonal antibody, chimeric antibody, or antigen binding fragment thereof specifically binds GPIbα.

2. A method of treating human platelets, comprising obtaining human platelets, and
contacting the human platelets with the monoclonal antibody, the humanized monoclonal antibody, the chimeric antibody, or the antigen binding fragment of claim 1, thereby treating the human platelets.

3. The monoclonal antibody of claim 1, wherein the $V_H$ region comprises the amino acid sequence of SEQ ID NO. 6 and the $V_L$ region comprises the amino acid sequence of SEQ ID NO. 12.

4. A platelet storage solution comprising the monoclonal antibody, humanized monoclonal antibody, chimeric antibody, or antigen binding fragment of claim 1.

5. A pharmaceutical composition comprising the monoclonal antibody, humanized monoclonal antibody, chimeric antibody, or antigen binding fragment of claim 1, and a pharmaceutically acceptable carrier.

6. A method of inhibiting ectodomain shedding of GPIbα by platelets, comprising:
contacting the platelets with the monoclonal antibody, the humanized monoclonal antibody, the chimeric antibody, or the antigen binding fragment of claim 1, thereby inhibiting ectodomain shedding of GPIbα by the platelets.

7. The humanized monoclonal antibody of claim 1.

8. The chimeric antibody of claim 1.

9. The antigen binding fragment of claim 1.

10. An anti-GPIbα monoclonal antibody, humanized monoclonal antibody, chimeric antibody, or antigen binding fragment thereof, comprising a) a $V_H$ region comprising three heavy chain CDRs and b) a $V_L$ region comprising three light chain CDRs,
wherein the three light chain CDRs are:
light chain CDR1: RASGNIHNYLA (SEQ ID NO. 33);
light chain CDR2: NAETLAD (SEQ ID NO. 38); and
light chain CDR3: QHFWDTPWT (SEQ ID NO. 42);
wherein the three heavy chain CDRs are:
heavy chain CDR1: TSNMGVV (SEQ ID NO. 21);
heavy chain CDR2: HILWNDGKFYNPALKS (SEQ ID NO. 24); and
heavy chain CDR3: LFSTTTSGYFDV (SEQ ID NO. 27),
and wherein the monoclonal antibody, humanized monoclonal antibody, chimeric antibody, or antigen binding fragment thereof specifically binds GPIbα.

11. A method of treating human platelets, comprising obtaining human platelets, and
contacting the human platelets with the monoclonal antibody, the humanized monoclonal antibody, the chimeric antibody, or the antigen binding fragment of claim 10, thereby treating the human platelets.

12. The monoclonal antibody (mAb) of claim 10, wherein the $V_H$ region comprises the amino acid sequence of SEQ ID NO. 5 and the $V_L$ region comprises the amino acid sequence of SEQ ID NO. 11.

13. A platelet storage solution comprising the monoclonal antibody, the humanized monoclonal antibody, the chimeric antibody, or the antigen binding fragment of claim 10.

14. A pharmaceutical composition comprising the monoclonal antibody, the humanized monoclonal antibody, the chimeric antibody, or the antigen binding fragment of claim 10, and a pharmaceutically acceptable carrier.

15. A method of inhibiting ectodomain shedding of GPIbα by platelets, comprising:
  contacting the platelets with the monoclonal antibody, the humanized monoclonal antibody, the chimeric antibody, or the antigen binding fragment of claim 10,
  thereby inhibiting ectodomain shedding of GPIbα by the platelets.

16. The humanized monoclonal antibody of claim 10.
17. The chimeric antibody of claim 10.
18. The isolated antigen binding fragment of claim 10.

* * * * *